(12) United States Patent
Aoki

(10) Patent No.: US 11,678,817 B2
(45) Date of Patent: Jun. 20, 2023

(54) POSTURE ESTIMATION DEVICE, POSTURE ESTIMATION METHOD, AND STORAGE MEDIUM

(71) Applicant: HONDA MOTOR CO., LTD., Tokyo (JP)

(72) Inventor: Haruo Aoki, Wako (JP)

(73) Assignee: HONDA MOTOR CO., LTD., Tokyo (JP)

( * ) Notice: Subject to any disclaimer, the term of this patent is extended or adjusted under 35 U.S.C. 154(b) by 527 days.

(21) Appl. No.: 16/881,047

(22) Filed: May 22, 2020

(65) Prior Publication Data

US 2020/0383609 A1   Dec. 10, 2020

(30) Foreign Application Priority Data

Jun. 10, 2019 (JP) .............................. JP2019-108105

(51) Int. Cl.
*A61B 5/11* (2006.01)
*A61B 5/107* (2006.01)
*G01C 25/00* (2006.01)

(52) U.S. Cl.
CPC .......... *A61B 5/1116* (2013.01); *A61B 5/1071* (2013.01); *G01C 25/00* (2013.01)

(58) Field of Classification Search
CPC ............................... A61B 5/1116; A61B 5/112
See application file for complete search history.

(56) References Cited

U.S. PATENT DOCUMENTS

| 2006/0161363 | A1 | 7/2006 | Shibasaki et al. |
| 2015/0193003 | A1 | 7/2015 | Yamada |
| 2015/0193014 | A1 | 7/2015 | Yamada |

FOREIGN PATENT DOCUMENTS

| CN | 106908021 | | 6/2017 |
| CN | 106908021 A | * | 6/2017 |

(Continued)

OTHER PUBLICATIONS

Japanese Office Action for Japanese Patent Application No. 2019-108105 dated Oct. 4, 2022.

(Continued)

*Primary Examiner* — Herbert K Roberts
(74) *Attorney, Agent, or Firm* — Amin, Turocy & Watson, LLP

(57) ABSTRACT

A posture estimation device includes an acquisition part acquires information of angular velocities and accelerations from a plurality of sensors that detects angular velocities and accelerations and that are attached to a plurality of locations on an estimation object, a conversion part that converts information acquired by the acquisition part into information of a standard coordinate system from a sensor coordinate system, an integrating part that calculates an orientation of a reference area of the estimation object as a part of a posture of the estimation object by integrating the converted angular velocities, and a correction part, assuming a representative plane passing through a reference area included in the estimation object, corrects the converted angular velocities of the reference area so that a normal line of the representative plane and an orientation of the reference area calculated by the integrating part approaches to directions that are perpendicular to each other.

5 Claims, 14 Drawing Sheets

Twisting
$v_i \cdot n > 0$

(56) References Cited

FOREIGN PATENT DOCUMENTS

| JP | 2004-150900 | 5/2004 | | |
|----|-------------|--------|---|---|
| JP | 2004-264060 | 9/2004 | | |
| JP | 2004264060 A | * 9/2004 | ............... | A61B 5/11 |
| JP | 2017-023436 | 2/2017 | | |

OTHER PUBLICATIONS

Jonathan F S Lin et al: "Paper;Human pose, recovery using wireless inertial measurement units;Human pose recovery using wireless inertial measurement units", Physiological Measurement, Institute of Physics Publishing, Bristol, GB, vol. 33, No. 12, Nov. 23, 2012 (Nov. 23, 2012), pp. 2099-2115, XP020234074, ISSN: 0967-3334, DOI: 10.1088/0967-3334/33/12/2099.

Extended European Search Report for European Patent Application No. 20178694.4 dated Oct. 21, 2020.

Madgwick, et al. "Estimation of IMU and MARG orientation using a gradient descent alcorithm", 2011 IEEE International Conference on Rehabilitation Robotics, 2011.

Japanese Notice of Allowance for Japanese Patent Application No. 2019-108105 dated Jan. 10, 2023.

European Office Action for European Patent Application No. 20178694.4 dated Feb. 23, 2023.

* cited by examiner (1) OBJECTIVE FUNCTION OF PELVIS SEGMENT p ⋯ GRAVITY CORRECTION $$\min_{^S_E\hat{q}_p \in R^4} \frac{1}{2} \| f_g({}^S_E\hat{q}_p, {}^S\hat{a}_p) \|^2 \quad \cdots (A)$$

(2) OBJECTIVE FUNCTION OF SEGMENT i OTHER THAN PELVIS
⋯ GRAVITY CORRECTION AND REPRESENTATIVE PLANE CORRECTION $$\min_{^S_E\hat{q}_i \in R^4} \frac{1}{2} \{ c_i \| f_b({}^S_E\hat{q}_i, {}^S_E\hat{q}_p) \|^2 + \| f_g({}^S_E\hat{q}_i, {}^S\hat{a}_i) \|^2 \} \quad \cdots (B)$$

POSTURE ESTIMATION DEVICE, POSTURE ESTIMATION METHOD, AND STORAGE MEDIUM

CROSS-REFERENCE TO RELATED APPLICATION

Priority is claimed on Japanese Patent Application No. 2019-108105, filed Jun. 10, 2019, the content of which is incorporated herein by reference.

BACKGROUND OF THE INVENTION

Field of the Invention

The present invention relates to a posture estimation device, a posture estimation method, and a storage medium.

Description of Related Art

In the related art, a technology (motion capture) of estimating a body posture and a change (movement) thereof by attaching a plurality of inertial measurement unit (IMU) sensors (inertial measurement sensors) configured to measure an angular velocity and an acceleration to a body has been disclosed (for example, S. O. H. Madgwick, A. J. L. Harrison, and R. Vaidyanathan, "Estimation of IMU and MARG orientation using a gradient descent algorithm" in 2011 IEEE International Conference on Rehabilitation Robotics, 2011). In general, the angular velocity measured by the IMU sensors includes noise or a bias error, and an accurate posture cannot be calculated through simple integration. Here, in many posture estimation technologies, estimation accuracy is improved by performing correction in a roll axis direction and a pitch axis direction using acceleration.

SUMMARY OF THE INVENTION

However, in a technique of the related art, correction in a yaw direction cannot be performed using only acceleration. For this reason, in a motion capture system using a conventional IMU sensor, in addition to an angular velocity and an acceleration, an azimuth is measured by a geomagnetic sensor, and correction in a yaw direction is generally performed. However, since geomagnetism is easily disturbed due to an influence of buildings, furniture, or the like, formed of metal, an environment in which correction in a yaw direction operates normally is limited. In particular, in measurement over a long time, disturbance of geomagnetism has a large influence on estimation accuracy in a yaw direction. When an error in the yaw direction is high, body areas (segments) are twisted in different directions, which is unnatural for a person's whole body posture. In the technique of the related art, while there is a function of correcting unnatural joint displacement or posture in processing after measurement, this takes time for processing and sometimes it cannot be corrected in real time.

An aspect of the present invention is directed to providing a posture estimation device, a posture estimation method, and a storage medium that are capable of more accurate posture estimation.

A posture estimation device, a posture estimation method, and a storage medium according to the present invention employ the following configurations.

(1) A posture estimation device according to an aspect of the present invention includes: an acquisition part that is configured to acquire information of angular velocities and accelerations from a plurality of sensors configured to detect angular velocities and accelerations, the plurality of sensors being attached to a plurality of locations on an estimation object which is a human, an animal, or a robot having joints with a limited motion range; a conversion part configured to convert information acquired by the acquisition part into information of a standard coordinate system from a sensor coordinate system; an integrating part configured to calculate an orientation of a reference area of the estimation object to which the sensors are attached as a part of a posture of the estimation object by integrating the converted angular velocities; and a correction part, assuming a representative plane passing through the reference area included in the estimation object, configured to correct the converted angular velocities of the reference area so that a normal line of the representative plane and an orientation of the reference area calculated by the integrating part approaches to directions that are perpendicular to each other.

(2) In the aspect of the above-mentioned (1), processing of the integrating part and the correction part may be repeatedly performed in each processing cycle, and the correction part may increase a degree of correcting the converted angular velocity of the reference area according to a continuation of a separation of an orientation of the reference area, which is calculated by the integrating part in the previous processing cycle, from an orientation which is perpendicular with respect to a normal line of the representative plane.

(3) In the aspect of the above-mentioned (1) or (2), the correction part may correct the converted angular velocity of the reference area so as to reduce an inner product of the normal line of the representative plane and the orientation of the reference area calculated by the integrating part.

(4) In the aspect of any one of the above-mentioned (1) to (3), the correction part may further correct the converted angular velocity of the reference area so as to reduce a separation between (i) an assumed gravity acceleration direction of each reference area derived from an orientation of the calculated reference area by the integrating part and (ii) a measured gravity acceleration direction of each reference area recognized on the basis of information of an acceleration acquired by the acquisition part.

(5) A posture estimation method according to an aspect of the present invention performed by a computer, the method including: acquiring information of angular velocities and accelerations from a plurality of sensors that are attached to a plurality of locations on an estimation object which is a human, an animal, or a robot having joints with a limited motion range and that are configured to detect angular velocities and accelerations; converting the acquired information into information of a standard coordinate system from a sensor coordinate system; calculating an orientation of a reference area of the estimation object to which the sensors are attached as a part of a posture of the estimation object by integrating the converted angular velocities; and assuming a representative plane passing through a reference area included in the estimation object and correcting the converted angular velocities of the reference area so that a normal line of the representative plane and an orientation of the calculated reference area approaches to directions that are perpendicular to each other.

(6) A storage medium according to an aspect of the present invention, on which a program is stored, and configured to cause a computer to: acquire information of angular velocities and accelerations from a plurality of sensors that are attached to a plurality of locations on an estimation object which is a human, an animal, or a robot having joints with a limited motion range and that are configured to detect angular velocities and accelerations; convert the acquired information into information of a standard coordinate system from a sensor coordinate system; calculate an orientation of a reference area of the estimation object to which the sensors are attached as a part of a posture of the estimation object by integrating the converted angular velocities; and assume a representative plane passing through a reference area included in the estimation object and correct the converted angular velocities of the reference area so that a normal line of the representative plane and an orientation of the calculated reference area approaches to directions that are perpendicular to each other.

According to the aspects of the above-mentioned (1) to (6), even in an environment in which the IMU sensor is likely to be affected by an influence of magnetism, more accurate posture estimation can be performed.

In addition, according to the aspects of the above-mentioned (2) to (4), when a state in which the measurement object rotates some segments in the yaw angle direction is continued, correction can be made assuming that the rotation will be canceled out.

DETAILED DESCRIPTION OF THE INVENTION

Hereinafter, an embodiment of a posture estimation device, a posture estimation method, and a storage medium of the present invention will be described with reference to the accompanying drawings.

[Entire Configuration]

Figure 1:
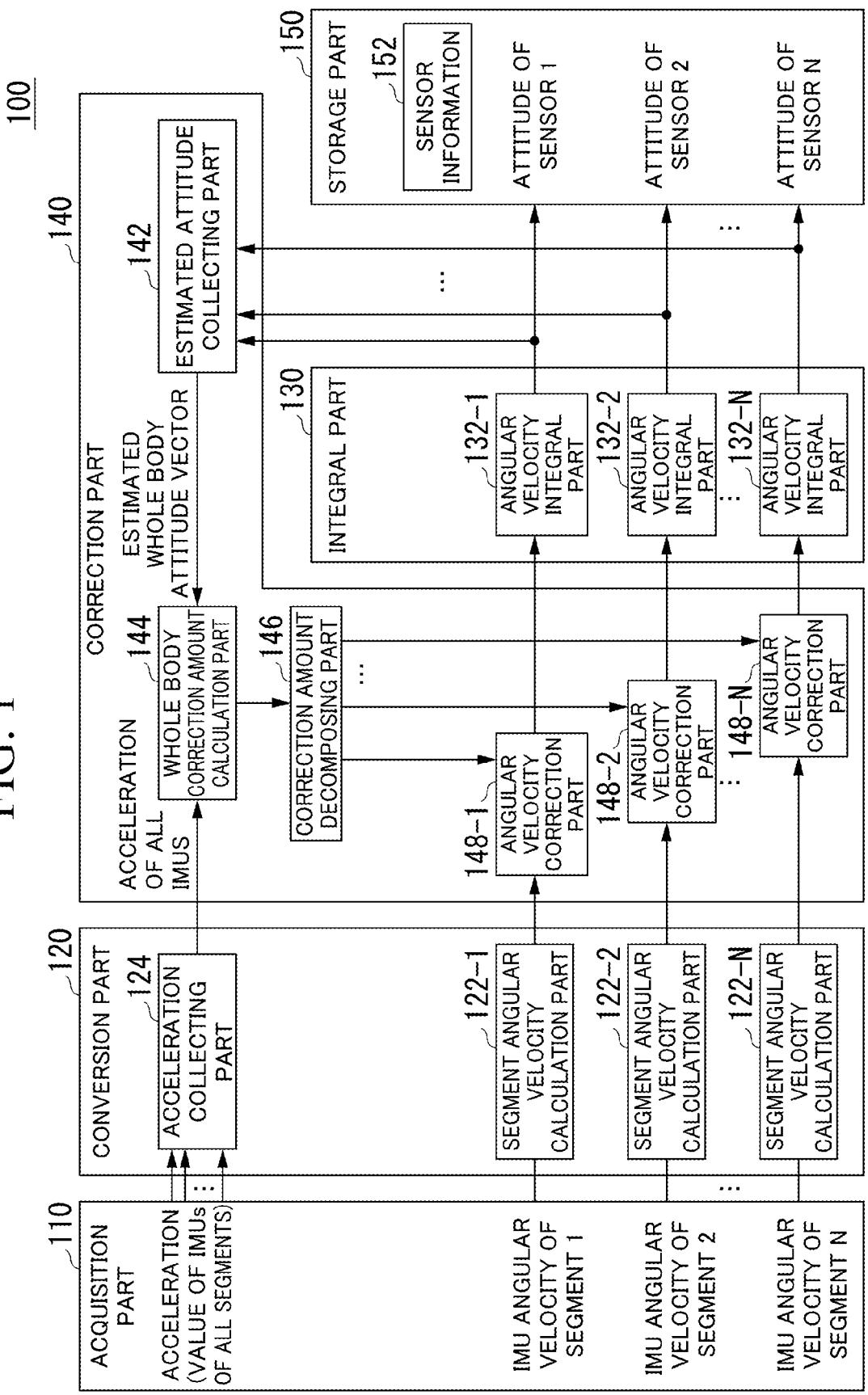
FIG. 1 is a configuration view of a posture estimation device of an embodiment.

FIG. 1 is a configuration view of a posture estimation device 100 of an embodiment. The posture estimation device 100 includes, for example, an acquisition part 110, a conversion part 120, an integrating part 130, a correction part 140 and a storage part 150. Components (except the storage part 150) of the posture estimation device 100 are realized by, for example, executing a program using a processor such as a central processing unit (CPU) or the like. In addition, some or all of these may be realized by hardware such as a large scale integration (LSI), an application specific integrated circuit (ASIC), a field-programmable gate array (FPGA), or the like, or may be realized by cooperation of software and hardware.

A program may have been previously stored in a storage device (a storage device including a non-transient storage medium) such as an HDD, a flash memory, or the like, or may be stored in a detachable storage medium (a non-transient storage medium) such as a DVD, a CD-ROM, or the like, and the storage medium may be installed by being mounted on a drive device.

Processing by the acquisition part 110, the conversion part 120, the integrating part 130, and the correction part 140 is repeatedly performed in each processing cycle. For example, the correction part 140 derives a correction amount on the basis of the processed result of the integrating part 130 of the previous processing cycle, and reflects the derived correction amount in the integrating part 130 in the current processing cycle.

The acquisition part 110 is attached to a plurality of locations on an estimation object that is, for example, a human, an animal, or a robot having a limited range of motion of a joint, and acquires information an angular velocity and acceleration from a plurality of IMU sensors configured to detect an angular velocity and acceleration. The acquisition part 110 is connected communicatively to the IMU sensors in, for example, a wired or wireless manner and able to communicate with the IMU sensors. The acquisition part 110 outputs an acquired result to the conversion part 120.

Figure 2:
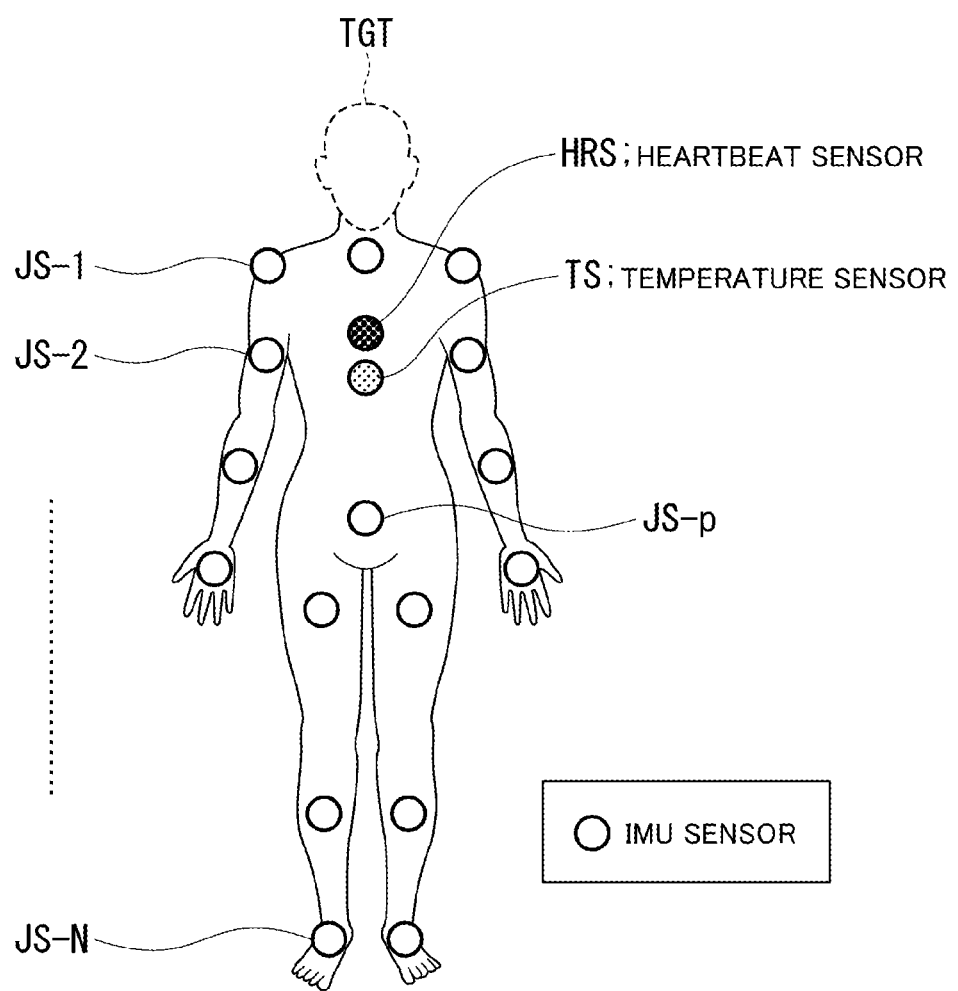
FIG. 2 is a view for explaining IMU sensors.

FIG. 2 is a view for describing the IMU sensors. When an estimation object TGT is a person, IMU sensors JS-1 to JS-N(N is a total number of IMU sensors) are attached to a plurality of spots such as the head, the chest, around the pelvis, left and right hands and legs, and the like, of the person. Hereinafter, if there is no particular distinction between the IMU sensors, reference signs after a hyphen will be omitted and they will simply be referred to as the IMU sensors JS. In addition, a parameter i is adopted for the meaning of any one of 1 to N, and the IMU sensor JS-i or the like are referred to. The IMU sensors JS are attached to a member (an IMU suit) such as removable clothes, and the IMU sensors JS are disposed at desired positions when the estimation object TGT is wearing the member. The IMU sensors JS can measure an angular velocity and an acceleration in three axes, respectively.

For example, the IMU sensors JS are disposed such that the IMU sensor JS-1 corresponds to a right shoulder, the IMU sensor JS-2 corresponds to a right upper arm, the IMU sensor JS-8 corresponds to a left thigh, and the IMU sensor JS-9 corresponds to a left below-knee region. In addition, the IMU sensor JS-p is attached to the surroundings of an area that becomes a reference area. When the estimation object is a person, the reference area corresponds to a part of a trunk of the body such as the pelvis or the like of the person. In the following description, one or more of the IMU sensors JS are attached, and each area of the object, movement of which is measured, is referred to as "a segment." The segment includes a reference area and an area to which a sensor is attached (hereinafter, referred to as a reference area) other than the reference area. Further, in addition to the IMU sensors JS, various sensors configured to acquire reference information posture estimation, such as a heartbeat sensor HRS, a temperature sensor TS, or the like, may be further attached to the IMU suit.

In the following description, components corresponding to the IMU sensors JS-1 to JS-N will be designated using reference signs, which will be appended after a hyphen.

Returning to FIG. 1, the conversion part 120 converts information acquired by the acquisition part 110 into information of a standard coordinate system from a 3-axis direction coordinate system (hereinafter, referred to as a sensor coordinate system) in each of the IMU sensors JS. The standard coordinate system is, for example, a ground coordinate system using a direction of gravity as one axis. The conversion part 120 outputs the converted result to the correction part 140. In addition, the conversion part 120 outputs the converted result to the integrating part 130 via the correction part 140.

The conversion part 120 includes, for example, a segment angular velocity calculation part 122-$i$ corresponding to each of segments, and an acceleration collecting part 124. The segment angular velocity calculation part 122-$i$ converts an angular velocity of the IMU sensor JS-$i$ output by the acquisition part 110 into information of the standard coordinate system. The result processed by the segment angular velocity calculation part 122-$i$ (on the basis of the result detected by the IMU sensors JS, information representing a posture of the estimation object TGT) is held, for example, in the form of a quaternion. Further, expression of the result measured by the IMU sensor JS-$i$ in the form of a quaternion is merely an example, and another expression method such as a rotating matrix or the like of a 3-dimensional rotation group SO3 may be used.

The acceleration collecting part 124 collects each acceleration detected by the IMU sensor JS-$i$ corresponding to the segment. The acceleration collecting part 124 converts the aggregate result into an acceleration of the whole body of the estimation object TGT (hereinafter, may be referred to as the entire IMU acceleration).

The integrating part 130 calculates an orientation of a segment (a reference area) of the estimation object TGT to which the IMU sensor JS-$i$ is attached as a part of a posture of the estimation object by integrating an angular velocity corresponding to the segment converted into the information of the standard coordinate system using the segment angular velocity calculation part 122-$i$. The integrating part 130 outputs the integrated result to the correction part 140 and the storage part 150.

When the processing cycle is the first cycle, the integration part 130 receives the angular velocity output by the conversion part 120 (an angular velocity that has not been corrected by the correcting part 140), and after that, the correcting part 140 described later inputs an angular velocity in which correction derived based on a processing result from the previous processing cycle has been reflected.

The integrating part 130 includes, for example, an angular velocity integrating part 132-$i$ corresponding to each segment. The angular velocity integrating part 132-$i$ calculates an orientation of the reference area of the estimation object, to which the IMU sensor JS-$i$ is attached, as a part of the posture of the estimation object by integrating an angular velocity of the segment output by the segment angular velocity calculation part 122-$i$.

The correction part 140 assumes a representative plane passing through the reference area included in the estimation object, and corrects the converted angular velocity of the reference area so that a normal line of a representative plane and an orientation of the reference area calculated by the integrating part 130 approaches to directions that are perpendicular to each other. The representative plane will be described below.

The correction part 140 includes, for example, an estimation posture aggregating part 142, a whole body correction amount calculation part 144, a correction amount decomposing part 146, and an angular velocity correction part 148-$i$ corresponding to each segment.

The estimation posture aggregating part 142 is configured to aggregate the quaternions that express the postures of each segment that are the results calculated by the angular velocity integrating part 132-$i$ into one vector. The aggregate vector is referred to as an estimated posture vector of the whole body.

The whole body correction amount calculation part 144 calculates a correction amount of the angular velocity of all segments on the basis of the entire IMU acceleration output by the acceleration collecting part 124 and the estimated posture vector of the whole body output by the estimation posture aggregating part 142. Further, the correction amount calculated by the whole body correction amount calculation part 144 is adjusted in consideration of a relation between the segments such that the posture of the whole body of the estimation object does not become unnatural. The whole body correction amount calculation part 144 outputs the calculated result to the correction amount decomposing part 146.

The correction amount decomposing part 146 decomposes the correction amount calculated by the whole body correction amount calculation part 144 as the correction amount of the angular velocity of each segment such that the correction amount calculated by the whole body correction amount calculation part 144 can be reflected in the angular velocity of each segment. The correction amount decomposing part 146 outputs the correction amount of the angular velocity of each of the decomposed segments to the angular velocity correction part 148-$i$ of the corresponding segment.

The angular velocity correction part 148-$i$ reflects the decomposed result of the correction amount of the angular velocity of the corresponding segment, which is output by the correction amount decomposing part 146, to the calculated result of the angular velocity of the corresponding segment which is output by the segment angular velocity calculation part 122-$i$. Accordingly, a target of integration as a processing target of the integrating part 130 in processing of the next cycle becomes an angular velocity in a state in which correction by the correction part 140 has been reflected.

The angular velocity correction part 148-$i$ corrects an angular velocity of the corresponding segment, which is output by the conversion part 120, by reflecting the result decomposed by the correction amount decomposing part 146 to the angular velocity of the corresponding segment which is output by the conversion part 120. The angular velocity correction part 148-$i$ outputs the corrected result to the angular velocity integrating part 132-$i$.

The storage part 150 includes, for example, a hard disk drive (HDD), a flash memory, an electrically erasable programmable read only memory (EEPROM), a read only memory (ROM), a random access memory (RAM), or the like, and stores various programs such as firmware, an application program, or the like, executed by a processor such as a CPU included in the posture estimation device 100, a result of processing executed by the processor, or the like. The storage part 150 stores, for example, the estimated result of the posture of each segment that is a result obtained from integrating by the integrating part 130, IMU sensor information 152, or the like. The IMU sensor information 152 is, for example, information related to the segments to which the plurality of IMU sensors JS are attached, a calibration program, or the like.

Further, the estimated result of the posture of each segment which is the result integrated by the integrating part 130 may be output to another device (an output display, a device configured to perform an arithmetic operation using an estimated result of the posture, or the like).

Figure 3:
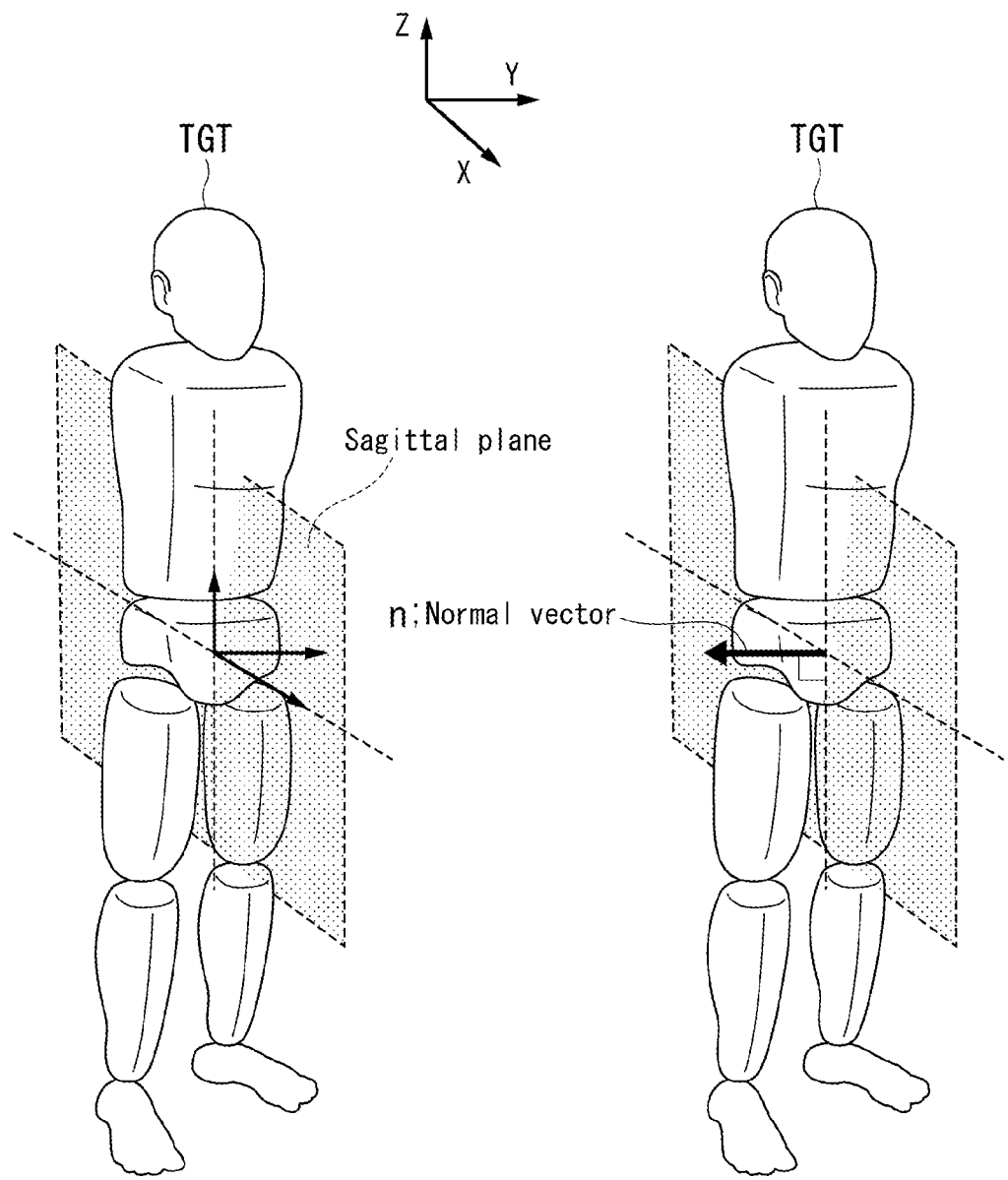
FIG. 3 is a view for describing planar assumption processing by a correction part.

FIG. 3 is a view for describing planar assumption processing by the correction part 140. The correction part 140 assumes a median sagittal plane passing through a center of the pelvis (a sagittal plane in the drawing) as a representative plane in a case the reference area is the pelvis of the estimation object as shown in the left drawing of FIG. 3. The median sagittal plane is a plane that divides the body into left and right areas and is parallel to the median of the body of the estimation object, which is laterally symmetrical. Further, the correction part 140 sets a normal line n (a normal vector which is an arrow in the drawing) of the assumed median sagittal plane as shown in a right view of FIG. 3.

Figure 4:
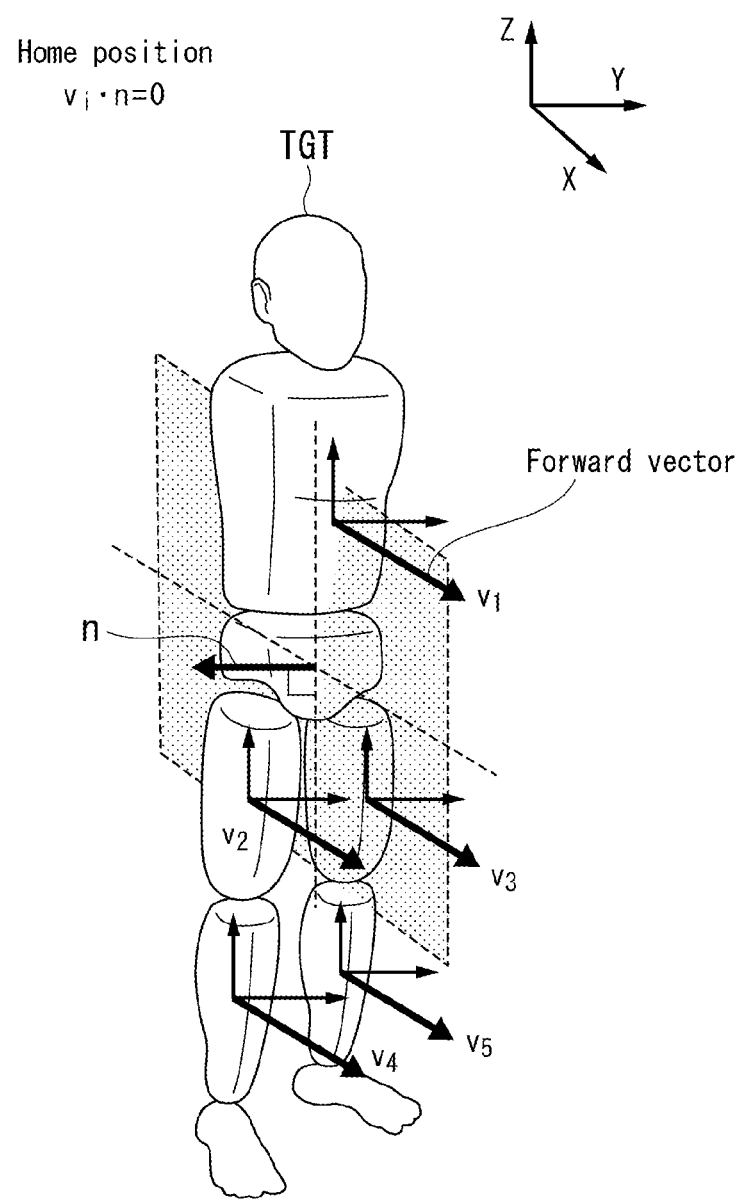
FIG. 4 is a view for describing definition processing of direction vectors by the correction part.

FIG. 4 is a view for describing definition processing of a direction vector vi by the correction part 140. The correction part 140 uses an output of a certain IMU sensor JS-i as an initial state, and defines an orientation thereof to be horizontal and parallel to the representative plane (calibration processing). After that, the direction vector turns in three directions according to rotation in the three directions obtained by integrating the output of the IMU sensor JS-i.

As shown in FIG. 4, when the chest, left and right thigh sections, and left and right below-knee regions are included in the reference area of the estimation object TGT, the correction part 140 performs estimation of the attachment posture of the IMU sensors JS on the basis of the result of the calibration processing, corrects the converted angular velocities of the reference area so that the normal line n and an orientation of the reference area which is calculated by the integrating part 130 approaches to directions that are perpendicular to each other, and derives direction vectors v1 to v5 (forward vectors in the drawings) facing the reference area as shown. As shown, the direction vector v1 designates a direction vector of the chest, the direction vectors v2 and v3 designate direction vectors of the thigh sections, and the direction vectors v4 and v5 designate direction vectors of the below-knee regions. Further, an x axis, a y axis and a z axis in the drawings are examples of directions of the standard coordinate system.

Figure 5:
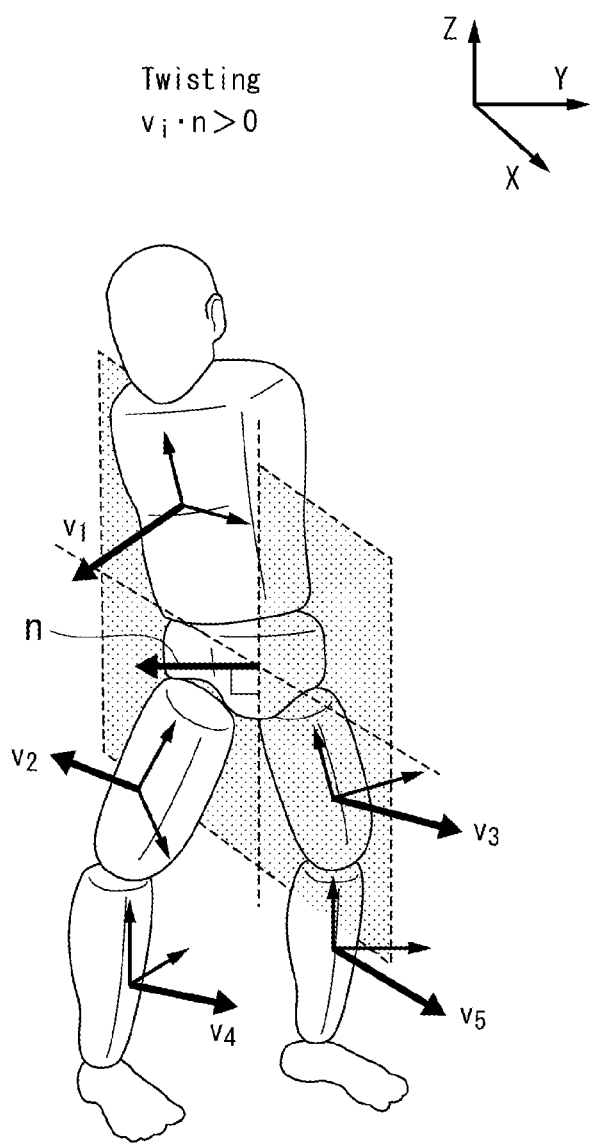
FIG. 5 is a view showing an aspect in which the direction vectors are turned.

FIG. 5 is a view showing an aspect in which the direction vector vi is turned according to a posture change of the estimation object. The representative plane turns in a yaw direction according to the displacement in the yaw direction obtained by integrating the output of the IMU sensor JS-p in a case the output of the IMU sensor JS-p in the certain reference area is set as an initial state. The correction part 140 increases a degree of correction of the converted angular velocity of the reference area according to a continuation of a separation of the orientation of the reference area, which is calculated by the integrating part 130 in the previous cycle, from the orientation which is perpendicular with respect to the normal line n of the median sagittal plane.

[Estimation of Posture]

For example, as shown in FIG. 4, in a case an inner product between the direction vector vi of the reference area and the normal line n is 0, the correction part 140 determines that the orientation of the reference area is a posture at a home position that is not separated from the orientation perpendicular with respect to the normal line n of the median sagittal plane. In a case the inner product between the direction vector vi and the normal line n is larger than 0 as shown in FIG. 5, the correction part 140 determines that the orientation of the reference area is separated from the orientation perpendicular to the normal line n of the median sagittal plane. The home position is a basic posture of the estimation object TGT (however, relative to the representative plane) which is acquired as the result of the calibration processing after the IMU sensors JS are attached to the estimation object TGT, for example, a vertical standstill state. Accordingly, the calibration processing is processing of performing definition of the home position on the basis of the results measured by the IMU sensors JS obtained by performing a predetermined operation (a calibration operation) on the estimation object TGT.

Accordingly, the correction part 140 performs the correction reflecting that the separation is reduced as a time elapses (for example, approaching the home position shown in a right view of FIG. 5) on the basis of assumption that the posture in which the estimation object is separated from the orientation perpendicular to the normal line n of the median sagittal plane (i.e., a state in which the body is twisted as shown in a left view of FIG. 5) is continued for a long time is rare, or making movements while maintaining the posture separated from the orientation perpendicular to the normal line n of the median sagittal plane is rare.

Figure 6:
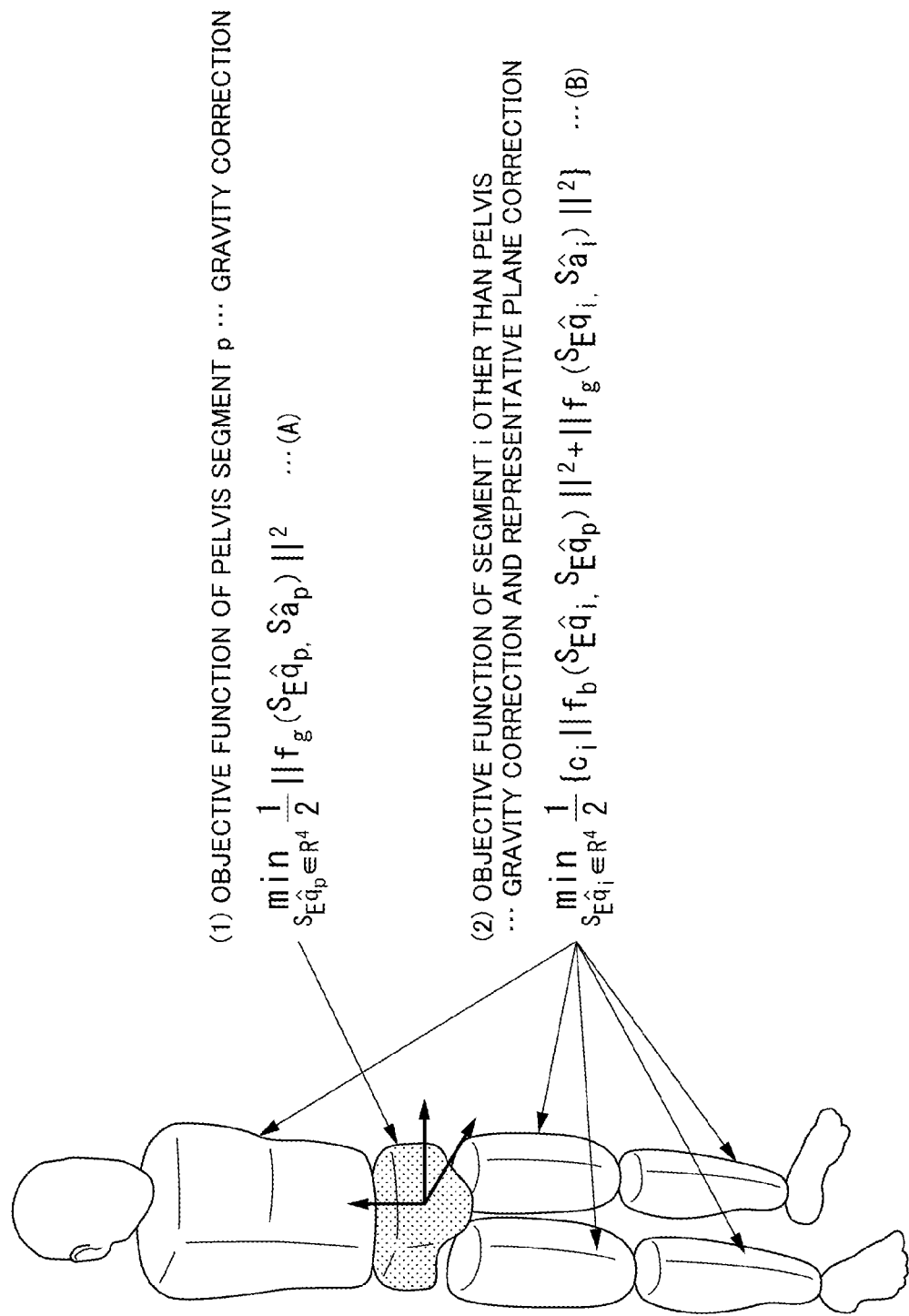
FIG. 6 is a view illustrating a summary of correction processing by a posture estimation device.

FIG. 6 is a view for describing summary of correction processing by the posture estimation device 100. The posture estimation device 100 defines optimization problems that are different in the pelvis and other segments of the estimation object TGT. First, the posture estimation device 100 calculates a posture of the pelvis of the estimation object TGT, and calculates postures of the other segments using the posture of the pelvis.

As shown in FIG. 6, if the calculation of the pelvis posture (objective function of pelvis segment p, mathematical equation (A), gravity correction) and the calculation of postures of segments other than the pelvis (objective function of segment i other than pelvis, mathematical equation (B), gravity correction & representative plane correction) are performed separately, the posture of the pelvis will be estimated using only gravity correction. In the posture estimation device 100, the estimation of the posture of the pelvis and the estimation of the postures of the other segments are simultaneously performed, with an aim of optimization in consideration of the influence of all the IMU sensors JS such that estimation of the posture of the pelvis can be performed also in consideration of the postures of the other segments.

[Math. A]

$$\min_{S_E\hat{q}_p \in R^4} \frac{1}{2}\|f_g(S_E\hat{q}_p, S_{\tilde{a}_p})\|^2 \tag{A}$$

[Math. B]

$$\min_{S_E\hat{q}_i \in R^4} \frac{1}{2}\{c_i\|f_b(S_E\hat{q}_i, S_E\hat{q}_p)\|^2 + \|f_g(S_E\hat{q}_i, S_{\tilde{a}_i})\|^2\} \tag{B}$$

[Example of Arithmetic Operation]

Hereinafter, an example of a specific arithmetic operation upon estimation of a posture will be described according to mathematical equation shown.

A method of expressing a quaternion in order to express a posture will be described. When rotation from a frame A to a frame B of a certain coordinate system is represented by a quaternion, the following mathematical equation (1) is obtained. However, the frame B is rotated by θ about an axis normalized to the frame A.

[Math. 1]

$$^A_B\hat{q} = [q_1 \quad q_2 \quad q_3 \quad q_4]^T = \left[\cos\frac{\theta}{2} \quad -r_x\sin\frac{\theta}{2} \quad -r_y\sin\frac{\theta}{2} \quad -r_z\sin\frac{\theta}{2}\right]^T \quad (1)$$

Further, in the following description, a quaternion q with a hat symbol (a unit quaternion that expresses rotation) will be described as "q(h)." The unit quaternion is a quaternion divided by a norm. q(h) is a column vector having four actual number elements as expressed in Equation (1). When an estimated posture vector Q of a whole body of the estimation object TGT is expressed using an expression method, this can be shown as the following mathematical equation (2).

[Math. 2]

$$Q = \begin{bmatrix} ^S_E\hat{q}_p \\ ^S_E\hat{q}_1 \\ ^S_E\hat{q}_2 \\ \vdots \\ ^S_E\hat{q}_i \\ \vdots \\ ^S_E\hat{q}_N \end{bmatrix} \in \mathbb{R}^{4(N+1)} \quad (2)$$

Further, $^S_E q(h)$ (i is an integer number of 1 to N designating segments, or p designating a reference position) expresses rotation from a reference position of the IMU sensors JS of the reference area in a coordinate system S (a segment coordinate system) to a reference coordinate position E (for example, a coordinate system that can be defined from a gravity direction of the Earth) as a quaternion. The estimated posture vector Q of the whole body of the estimation object TGT is a column vector having 4(N+1) actual number elements, which unites unit quaternions representing postures of all segments as one.

In order to estimate the posture of the estimation object TGT, first, posture estimation of one segment to which the IMU sensors JS are attached is considered.

[Math. 3]

$$\min_{^S_E\hat{q}\in\mathbb{R}^4} \frac{1}{2}\|f(^S_E\hat{q}, ^E\hat{d}, ^S\hat{s})\|^2 \quad (3)$$

$$f(^S_E\hat{q}, ^E\hat{d}, ^S\hat{s}) = ^S_E\hat{q}^* \otimes ^E\hat{d} \otimes ^S_E\hat{q} - ^S\hat{s} \quad (4)$$

$^S_S\hat{q}=[q_1 q_2 q_3 q_4]$:Estimated*IMU* posture(sensor coordinate system) (5)

$^S\hat{d}=[0 d_x d_y d_x]$:Direction of reference such as gravity, geomagnetism, or the like(constant/reference coordinate system) (6)

$^S\hat{s}=[0 s_x s_y s_z]$:Measured value of reference such as gravity,geomagnetism or the like(sensor coordinate system) (7)

Mathematical equation (3) is an example of an updated equation of an optimization problem, and is an equation for deriving a correction amount in a roll/pitch direction by deriving a minimum value of ½ of a norm of a derived result of a function expressed in Mathematical equation (4). A right side of Mathematical equation (4) is an equation subtracting a standard direction, which is measured by the IMU sensors JS expressed by the sensor coordinate system, from information showing a direction in which a standard obtained from an estimation posture expressed by the sensor coordinate system (for example, a direction of gravity, geomagnetism, or the like) supposed to be present.

As expressed in Mathematical equation (5), the equation is an example in which a unit quaternion $^S_E q(h)$ is expressed in a matrix form. In addition, as expressed in Mathematical equation (6), $^E d(h)$ is a vector showing a standard direction used to correct a yaw direction (for example, a direction of gravity, geomagnetism, or the like). In addition, as expressed in Mathematical equation (7), $^S s(h)$ is a vector showing a standard direction which is measured by the IMU sensors JS expressed by the sensor coordinate system.

Further, when the gravity is used for a standard, Mathematical equation (6) and Mathematical equation (7) can be expressed as the following Mathematical equation (8) and Mathematical equation (9). $a_x$, $a_y$, and $a_z$ express an acceleration in an x-axis direction, an acceleration in a y-axis direction, and an acceleration in a z-axis direction, respectively.

$$^E d(h)=[0\ 0\ 0\ 1] \quad (8)$$

$$^S s(h)=[0 a_x a_y a_z] \quad (9)$$

A relational equation expressed in Mathematical equation (3) can be solved by, for example, a gradient descent method. In this case, an updated equation of an estimation posture can be expressed in Mathematical equation (10). In addition, a gradient of an objective function is expressed using the following Mathematical equation (11). In addition, Mathematical equation (11) expressing the gradient can be calculated using Jacobian as expressed in Mathematical equation (12). Further, Jacobian expressed in Mathematical equation (12) is a matrix in which a gravity error term and an error term in a yaw direction are partially differentiated by each element of the direction vector vi of the whole body. The gravity error term and the error term in the yaw direction will be described below.

[Math. 4]

$$^S_E\hat{q}_{k+1} = ^S_E\hat{q}_k - \mu\nabla\left\{\frac{1}{2}\|f(^S_E\hat{q}, ^E\hat{d}, ^S\hat{s})\|^2\right\}, \quad (10)$$

$$k = 0, 1, 2, \ldots$$

$$\nabla\left\{\frac{1}{2}\|f(^S_E\hat{q}, ^E\hat{d}, ^S\hat{s})\|^2\right\} = J^T(^S_E\hat{q}, ^E\hat{d})f(^S_E\hat{q}, ^E\hat{d}, ^S\hat{s}) \quad (11)$$

$$J(^S_E\hat{q}, ^E\hat{d}) = \begin{bmatrix} \frac{\partial f_1}{\partial q_1} & \frac{\partial f_1}{\partial q_2} & \frac{\partial f_1}{\partial q_3} & \frac{\partial f_1}{\partial q_4} \\ \frac{\partial f_2}{\partial q_1} & \frac{\partial f_2}{\partial q_2} & \frac{\partial f_2}{\partial q_3} & \frac{\partial f_2}{\partial q_4} \\ \frac{\partial f_3}{\partial q_1} & \frac{\partial f_3}{\partial q_2} & \frac{\partial f_3}{\partial q_3} & \frac{\partial f_3}{\partial q_4} \end{bmatrix} \quad (12)$$

As expressed on a right side of Mathematical equation (10), a unit quaternion $^S_E q(h)_{k+1}$ can be derived by subtracting a product of a coefficient μ (a fixed number of 1 or less) and the gradient from the unit quaternion $^S_E q(h)_k$ expressing the current estimation posture. In addition, as expressed in Mathematical equation (11) and Mathematical equation (12), the gradient can be derived as a relatively small calculation amount.

Further, an actual calculation example of Mathematical equation (4) and Mathematical equation (12) in a case the gravity is used for a standard is expressed in the following Mathematical equation (13) and Mathematical equation (14).

[Math. 5]

$$f_g(^S_E \hat{q}, {}^S \hat{a}) = \begin{bmatrix} 2(q_2 q_4 - q_1 q_3) - a_x \\ 2(q_1 q_2 - q_3 q_4) - a_y \\ 2\left(\dfrac{1}{2} - q_2^2 - q_3^2\right) - a_z \end{bmatrix} \quad (13)$$

$$J_g(^S_E \hat{q}) = \begin{bmatrix} -2q_3 & 2q_4 & -2q_1 & 2q_2 \\ 2q_2 & 2q_1 & 2q_4 & 2q_3 \\ 0 & -4q_2 & -4q_3 & 0 \end{bmatrix} \quad (14)$$

In the method expressed using Mathematical equations (3) to (7) and Mathematical equations (10) to (12) of the above-mentioned drawing, estimation of the posture can be performed by calculating the updated equation one time for each sampling. In addition, in a case the gravity is used for the standard to be exemplified in Mathematical equations (8), (9), (13) and (14), correction in a roll axis direction and a pitch axis direction can be performed.

[Whole Body Correction Amount Calculation]

Figure 7:
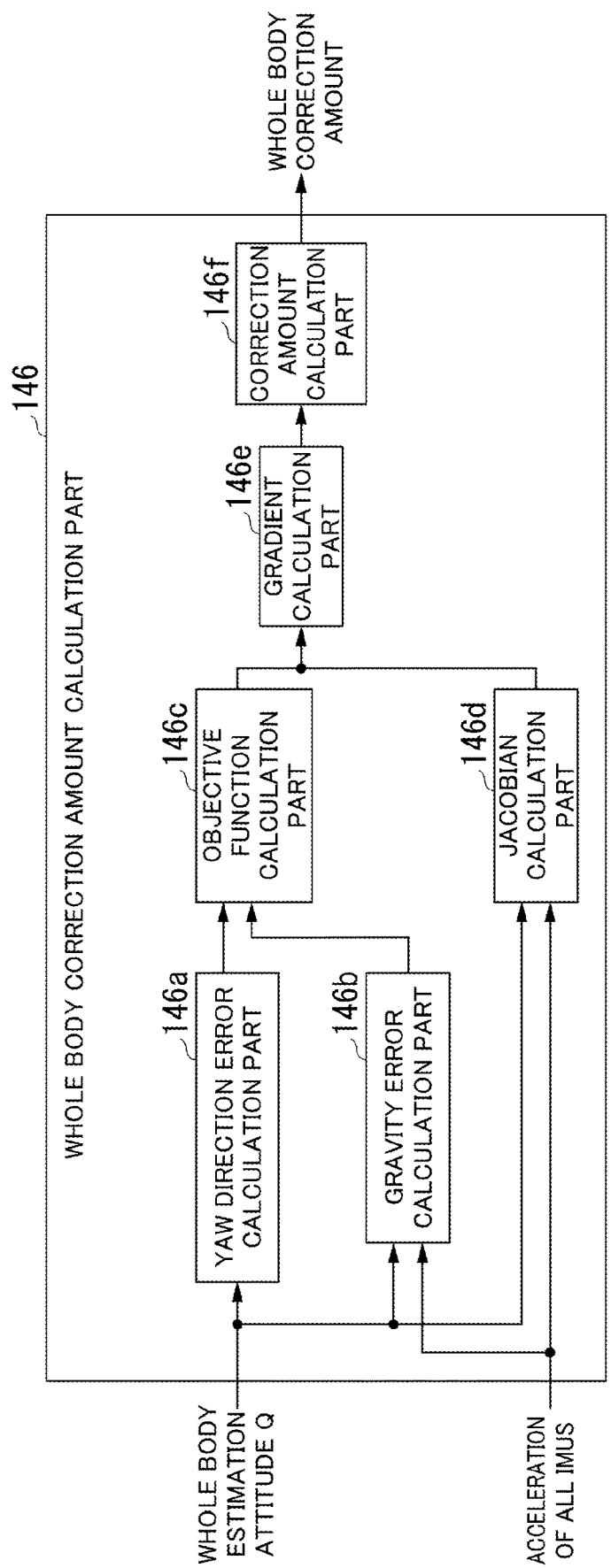
FIG. 7 is a view showing an example of a configuration of a whole body correction amount calculation part.

Hereinafter, a method of deriving a whole body correction amount (in particular, a correction amount in a yaw direction) with respect to an estimation posture will be described. FIG. 7 is a view showing an example of a configuration of the whole body correction amount calculation part 144. The whole body correction amount calculation part 144 includes, for example, a yaw direction error term calculation part 146a, a gravity error term calculation part 146b, an objective function calculation part 146c, a Jacobian calculation part 146d, a gradient calculation part 146e, and a correction amount calculation part 146f.

The yaw direction error term calculation part 146a calculates an error term in a yaw direction to realize correction in a yaw angle direction from the estimated posture of the whole body.

The gravity error term calculation part 146b calculates a gravity error term to realize correction in a roll axis direction and a pitch axis direction from the estimated posture of the whole body and the acceleration detected by the IMU sensors JS.

The objective function calculation part 146c calculates an objective function to correct the median sagittal plane and the direction vector vi of the estimation object TGT to become parallel to each other on the basis of the estimated posture of the whole body, the acceleration detected by the IMU sensors JS, the result calculated by the yaw direction error term calculation part 146a, and the result calculated by the gravity error term calculation part 146b. Further, a sum of squares of the gravity error term and the error term in a yaw direction is an objective function. The objective function will be described below in detail.

The Jacobian calculation part 146d calculates Jacobian obtained through partial differentiation of the estimated posture vector Q of the whole body from the estimation posture of the whole body and the acceleration detected by the IMU sensors JS.

The gradient calculation part 146e calculates a gradient by deriving a solution of an optimization problem using the result calculated by the objective function calculation part 146c and the result calculated by the Jacobian calculation part 146d.

The correction amount calculation part 146f derives a whole body correction amount applied to the estimated posture vector Q of the whole body of the estimation object TGT using the result calculated by the gradient calculation part 146e.

Figure 8:
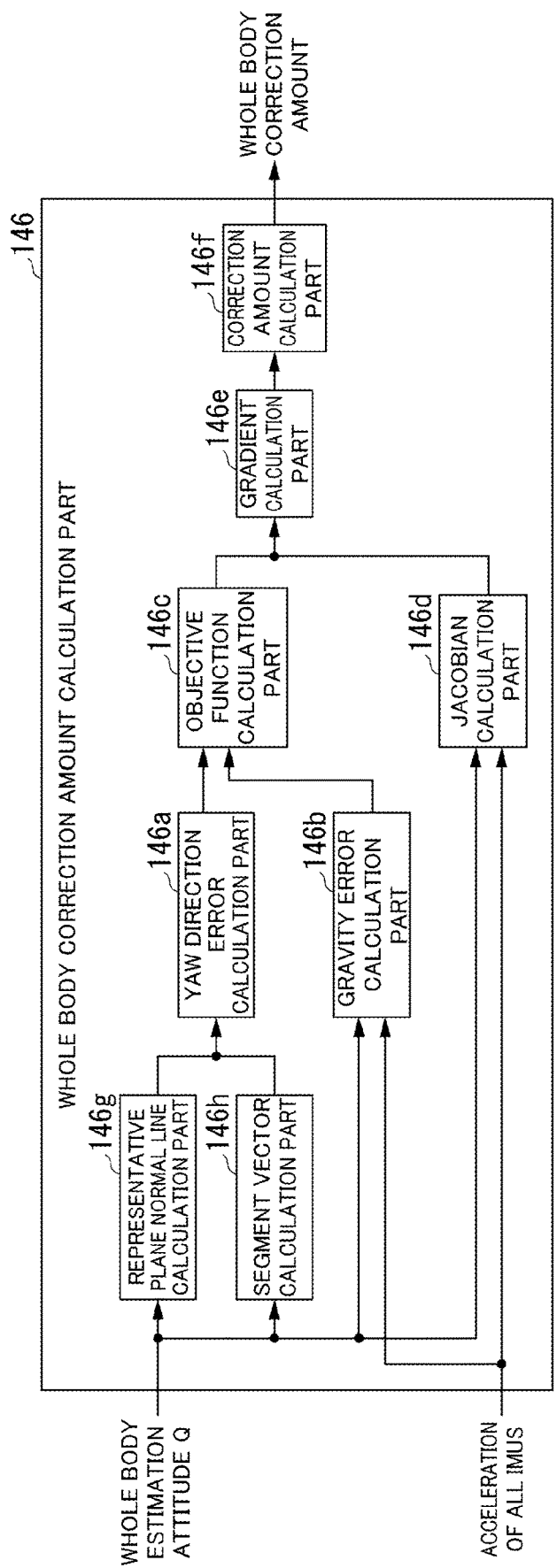
FIG. 8 is a view showing another example of the configuration of the whole body correction amount calculation part.

FIG. 8 is a view showing another example of a configuration of the whole body correction amount calculation part 144. The whole body correction amount calculation part 144 shown in FIG. 8 is configured to derive a whole body correction amount using the median sagittal plane and the direction vector vi of each segment, and further includes a representative plane normal line calculation part 146g and a segment vector calculation part 146h, in addition to the components shown in FIG. 7.

The representative plane normal line calculation part 146g calculates the normal line n of the median sagittal plane that is the representative plane on the basis of the whole body estimation posture. The segment vector calculation part 146h calculates the direction vector vi of the segment on the basis of the whole body estimation posture.

[Derived Example of Whole Body Correction Amount]

Hereinafter, a derived example of the whole body correction amount will be described.

The yaw direction error term calculation part 146a performs calculation of an inner product of an error term $f_b$ in a yaw direction to correct the median sagittal plane and the direction vector of the segment to be parallel to each other using Mathematical equation (15), which will be described below.

[Math. 6]

$$f_b({}^S_E \hat{q}_i, {}^S_E \hat{q}_p) = ({}^S_E \hat{q}_p \oplus {}^S n \oplus {}^S_E \hat{q}_p^*) \cdot ({}^S_E \hat{q}_i \oplus {}^S v_i \oplus {}^S_E \hat{q}_i^*) \in \mathbb{R} \quad (15)$$

The yaw direction error term $f_b$ is an equation that derives a correction amount on the basis of the unit quaternion $^S_E q(h)_i$ showing an estimation posture of a segment i and the unit quaternion $^S_E q(h)_p$ showing an estimation posture of the pelvis that is a reference area. A right side of Mathematical equation (15) is configured to derive an inner product of the normal line n of the median sagittal plane calculated by the representative plane normal line calculation part 146g and expressed by the sensor coordinate system and the direction vector vi of the segment calculated by the segment vector calculation part 146h and expressed by the sensor coordinate system. Accordingly, in a case the body of the estimation object TGT is in a twisted state, it is possible to perform correction in which the twist will be canceled (approaches the home position as shown in the right view of FIG. 5) is added to correction contents.

Next, the gravity error term calculation part 146b performs calculation to perform standard correction (for example, gravity correction) for each segment as shown in Mathematical equation (16).

[Math. 7]

$$f_g({}^S_E \hat{q}_i, {}^S \hat{a}_i) = {}^S_E \hat{q}_i^* \oplus {}^E \hat{d}_g \oplus {}^E_S \hat{q}_i - {}^S \hat{a}_i \quad (16)$$

Mathematical equation (16) is a relational equation between the unit quaternion $^S_E q(h)_i$ expressing the estimation posture of the arbitrary segment i and the acceleration (gravity) measured by the IMU sensor JS-i, and as shown on a right side of Mathematical equation (16), can be derived by subtracting the measured gravity direction (the measured gravity acceleration direction) $^S a_i(h)$ expressed by the sensor coordinate system from the direction in which the gravity obtained from the estimation posture and expressed by the sensor coordinate system is to be present (the assumed gravity acceleration direction).

Here, a specific example of the measured gravity direction $^S a_i(h)$ is expressed in Mathematical equation (17). In addition, a fixed number $^E d_g(h)$ showing the gravity direction can be expressed by the fixed number as shown in Mathematical equation (18).

[Math. 8]

$$^S \hat{a}_i = [0\, a_{i,x}\, a_{i,y}\, a_{i,z}]^T \quad (17)$$

$$^E \hat{d}_g = [0\ 0\ 0\ 1]^T \quad (18)$$

Next, objective function calculation part 146c calculates Mathematical equation (19) as the correction function of the segment i obtained by integrating the gravity error term and the error term in a yaw direction.

[Math. 9]

$$f_i(^S_E\hat{q}_i, ^S_E\hat{q}_p, ^S\hat{a}_i) = \begin{bmatrix} \sqrt{c_i}\, f_b(^S_E\hat{q}_i, ^S_E\hat{q}_p) \\ f_g(^S_E\hat{q}_i, ^S\hat{a}_i) \end{bmatrix} \in \mathbb{R}^4 \quad (19)$$

Here, $c_i$ is a weight coefficient of representative plane correction. Mathematical equation (19) showing the correction function of the segment i can be expressed as Mathematical equation (20) when formalized as an optimization problem.

[Math. 10]

$$\min_{^S_E\hat{q}_i \in \mathbb{R}^4} \frac{1}{2} \|f_b(^S_E\hat{q}_i, ^S_E\hat{q}_p, ^S\hat{a}_i)\|^2 \quad (20)$$

Further, Mathematical equation (20) is equivalent to Mathematical equation (21) of the correction function, which can be expressed as the sum of objective functions of the gravity correction and the representative plane correction.

[Math. 11]

$$\min_{^S_E\hat{q}_i \in \mathbb{R}^4} \frac{1}{2}\{c_i\|f_b(^S_E\hat{q}_i, ^S_E\hat{q}_p)\|^2 + \|f_g(^S_E\hat{q}_i, ^S\hat{a}_i)\|^2\} \quad (21)$$

The objective function calculation part 146c performs posture estimation similarly with respect to all the segments, and defines the optimization problem obtained by integrating the objective functions of the whole body. Mathematical equation (22) is a correction function $F(Q, \alpha)$ obtained by integrating the objective functions of the whole body. $\alpha$ is total IMU acceleration measured by the IMU sensors, and can be expressed as Mathematical equation (23).

[Math. 12]

$$F(Q, \alpha) = \begin{bmatrix} f_p(^S_E\hat{q}_p, ^S\hat{a}_p) \\ f_1(^S_E\hat{q}_1, ^S_E\hat{q}_p, ^S\hat{a}_1) \\ f_2(^S_E\hat{q}_2, ^S_E\hat{q}_p, ^S\hat{a}_2) \\ \vdots \\ f_i(^S_E\hat{q}_i, ^S_E\hat{q}_p, ^S\hat{a}_i) \\ \vdots \\ f_N(^S_E\hat{q}_N, ^S_E\hat{q}_p, ^S\hat{a}_N) \end{bmatrix} \in \mathbb{R}^{(3+4N)} \quad (22)$$

$$\alpha = \begin{bmatrix} ^S\hat{a}_p \\ ^S\hat{a}_1 \\ ^S\hat{a}_2 \\ \vdots \\ ^S\hat{a}_i \\ \vdots \\ ^S\hat{a}_N \end{bmatrix} \in \mathbb{R}^{4(N+1)} \quad (23)$$

Further, a first row on a right side of Mathematical equation (22) shows a correction function corresponding to the pelvis, and a second row and subsequent rows on the right side show correction functions corresponding to the other segments than the pelvis. An optimization problem for correcting a posture of the whole body of the estimation object TGT using the correction function expressed in Mathematical equation (22) can be defined as the following Mathematical equation (24). Mathematical equation (24) can be deformed as expressed in Mathematical equation (25) in the same type as Mathematical equation (21) that is the correction function of the previously mentioned segments.

[Math 13]

$$\min_{Q \in \mathbb{R}^{4(N+1)}} \frac{1}{2}\|F(Q, \alpha)\|^2 \quad (24)$$

$$\min_{Q \in \mathbb{R}^{4(N+1)}} \frac{1}{2}\left\{\|f_p(^S_E\hat{q}_p, ^S\hat{a}_p)\|^2 + \sum_{i=1}^{N} \|f_i(^S_E\hat{q}_i, ^S_E\hat{q}_p, ^S\hat{a}_i)\|^2\right\} \quad (25)$$

Next, the gradient calculation part 146e calculates a gradient of the objective function using Jacobian $J_F$ obtained through partial differentiation of the estimated posture vector Q of the whole body as expressed in the following Mathematical equation (26). Further, Jacobian $J_F$ is expressed in Mathematical equation (27).

[Math. 14]

$$\frac{1}{2}\nabla \|F(Q,\alpha)\|^2 = J_F^T(Q,\alpha)F(Q,\alpha) \tag{26}$$

$$J_F(Q,\alpha) = \begin{bmatrix} \dfrac{\partial f_p(^S_E\hat{q}_p, {}^S\hat{a}_p)}{\partial {}^S_E\hat{q}_p} & \dfrac{\partial f_p(^S_E\hat{q}_p, {}^S\hat{a}_p)}{\partial {}^S_E\hat{q}_1} & \cdots & \dfrac{\partial f_p(^S_E\hat{q}_p, {}^S\hat{a}_p)}{\partial {}^S_E\hat{q}_i} & \cdots & \dfrac{\partial f_p(^S_E\hat{q}_p, {}^S\hat{a}_p)}{\partial {}^S_E\hat{q}_N} \\ \dfrac{\partial f_1(^S_E\hat{q}_1, {}^S_E\hat{q}_p, {}^S\hat{a}_1)}{\partial {}^S_E\hat{q}_p} & \dfrac{\partial f_1(^S_E\hat{q}_1, {}^S_E\hat{q}_p, {}^S\hat{a}_1)}{\partial {}^S_E\hat{q}_1} & \cdots & \dfrac{\partial f_1(^S_E\hat{q}_1, {}^S_E\hat{q}_p, {}^S\hat{a}_1)}{\partial {}^S_E\hat{q}_i} & \cdots & \dfrac{\partial f_1(^S_E\hat{q}_1, {}^S_E\hat{q}_p, {}^S\hat{a}_1)}{\partial {}^S_E\hat{q}_N} \\ \vdots & \vdots & \ddots & \vdots & \ddots & \vdots \\ \dfrac{\partial f_i(^S_E\hat{q}_i, {}^S_E\hat{q}_p, {}^S\hat{a}_i)}{\partial {}^S_E\hat{q}_p} & \dfrac{\partial f_i(^S_E\hat{q}_i, {}^S_E\hat{q}_p, {}^S\hat{a}_i)}{\partial {}^S_E\hat{q}_1} & \cdots & \dfrac{\partial f_i(^S_E\hat{q}_i, {}^S_E\hat{q}_p, {}^S\hat{a}_i)}{\partial {}^S_E\hat{q}_i} & \cdots & \dfrac{\partial f_i(^S_E\hat{q}_i, {}^S_E\hat{q}_p, {}^S\hat{a}_i)}{\partial {}^S_E\hat{q}_N} \\ \vdots & \vdots & \ddots & \vdots & \ddots & \vdots \\ \dfrac{\partial f_N(^S_E\hat{q}_N, {}^S_E\hat{q}_p, {}^S\hat{a}_N)}{\partial {}^S_E\hat{q}_p} & \dfrac{\partial f_N(^S_E\hat{q}_N, {}^S_E\hat{q}_p, {}^S\hat{a}_N)}{\partial {}^S_E\hat{q}_1} & \cdots & \dfrac{\partial f_N(^S_E\hat{q}_N, {}^S_E\hat{q}_p, {}^S\hat{a}_N)}{\partial {}^S_E\hat{q}_i} & \cdots & \dfrac{\partial f_N(^S_E\hat{q}_N, {}^S_E\hat{q}_p, {}^S\hat{a}_N)}{\partial {}^S_E\hat{q}_N} \end{bmatrix} \in \mathbb{R}^{(3+4N)\times 4(N+1)} \tag{27}$$

Sizes of elements expressed in Mathematical equation (27) are become as the following Mathematical equations (28) and (29).

[Math. 15]

$$\frac{\partial f_p(^S_E\hat{q}_p, {}^S\hat{a}_p)}{\partial {}^S_E\hat{q}_p}, \frac{\partial f_p(^S_E\hat{q}_p, {}^S\hat{a}_p)}{\partial {}^S_E\hat{q}_i} \in \mathbb{R}^{3\times 4} \tag{28}$$

$$\frac{\partial f_i(^S_E\hat{q}_i, {}^S_E\hat{q}_p, {}^S\hat{a}_i)}{\partial {}^S_E\hat{q}_p}, \frac{\partial f_i(^S_E\hat{q}_i, {}^S_E\hat{q}_p, {}^S\hat{a}_i)}{\partial {}^S_E\hat{q}_i} \in \mathbb{R}^{4\times 4} \tag{29}$$

That is, while Jacobian $J_F$ expressed in Mathematical equation (27) becomes a large matrix of (3+4N)×4(N+1) (N is the number of all IMU sensors other than the IMU sensor for reference area measurement), actually, since elements expressed by the following Mathematical equations (30) and (31) are 0, the calculation can be omitted, and real time posture estimation becomes to be possible even with a slow arithmetic operation device.

[Math. 16]

$$\frac{\partial f_p(^S_E\hat{q}_p, {}^S\hat{a}_p)}{\partial {}^S_E\hat{q}_i} = 0, \forall_i \in [1, N] \tag{30}$$

$$\frac{\partial f_i(^S_E\hat{q}_i, {}^S_E\hat{q}_p, {}^S\hat{a}_i)}{\partial {}^S_E\hat{q}_j} = 0, i \neq j \tag{31}$$

When Mathematical equations (30) and (31) are substituted with the previously mentioned Mathematical equation (27), it can be expressed as the following Mathematical equation (32).

[Math. 17]

$$J_F(Q,\alpha) = \begin{bmatrix} \dfrac{\partial f_p(^S_E\hat{q}_p, {}^S\hat{a}_p)}{\partial {}^S_E\hat{q}_p} & 0 & \cdots & 0 & \cdots & 0 \\ \dfrac{\partial f_1(^S_E\hat{q}_1, {}^S_E\hat{q}_p, {}^S\hat{a}_1)}{\partial {}^S_E\hat{q}_p} & \dfrac{\partial f_1(^S_E\hat{q}_1, {}^S_E\hat{q}_p, {}^S\hat{a}_1)}{\partial {}^S_E\hat{q}_1} & \cdots & 0 & \cdots & 0 \\ \vdots & \vdots & \ddots & \vdots & \ddots & \vdots \\ \dfrac{\partial f_i(^S_E\hat{q}_i, {}^S_E\hat{q}_p, {}^S\hat{a}_i)}{\partial {}^S_E\hat{q}_p} & 0 & \cdots & \dfrac{\partial f_i(^S_E\hat{q}_i, {}^S_E\hat{q}_p, {}^S\hat{a}_i)}{\partial {}^S_E\hat{q}_i} & \cdots & 0 \\ \vdots & \vdots & \ddots & \vdots & \ddots & \vdots \\ \dfrac{\partial f_N(^S_E\hat{q}_N, {}^S_E\hat{q}_p, {}^S\hat{a}_N)}{\partial {}^S_E\hat{q}_p} & 0 & \cdots & 0 & \cdots & \dfrac{\partial f_N(^S_E\hat{q}_N, {}^S_E\hat{q}_p, {}^S\hat{a}_N)}{\partial {}^S_E\hat{q}_N} \end{bmatrix} \in \mathbb{R}^{(3+4N)\times 4(N+1)} \tag{32}$$

The gradient calculation part 146e can calculate a gradient expressed in Mathematical equation (26) using the result calculated by Mathematical equation (32).

[Processing Image of Whole Body Correction Amount Calculation Part]

Figure 9:
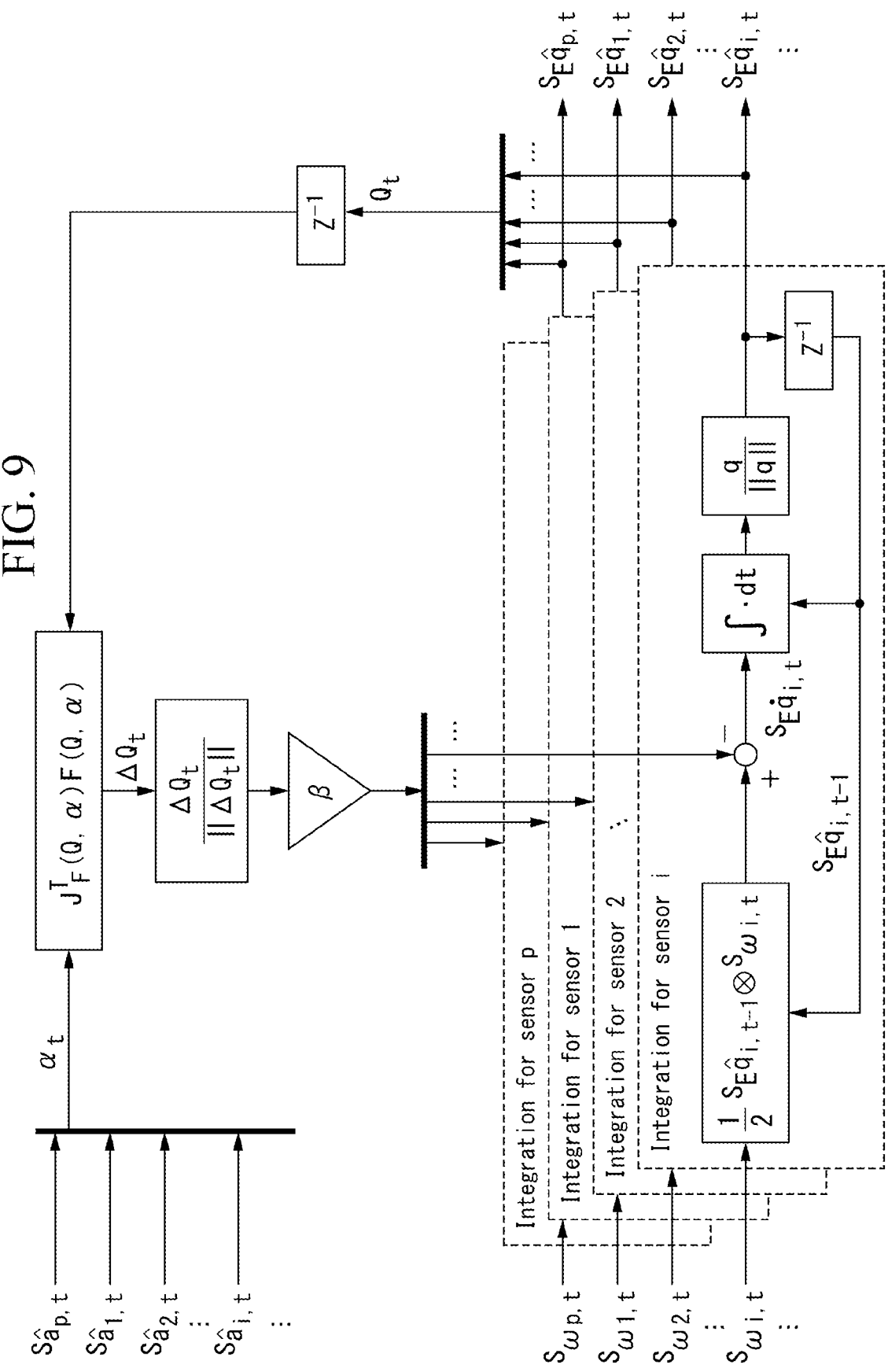
FIG. 9 is a view schematically showing a flow of an arithmetic operation processing of the whole body correction amount calculation part.
Figure 10:
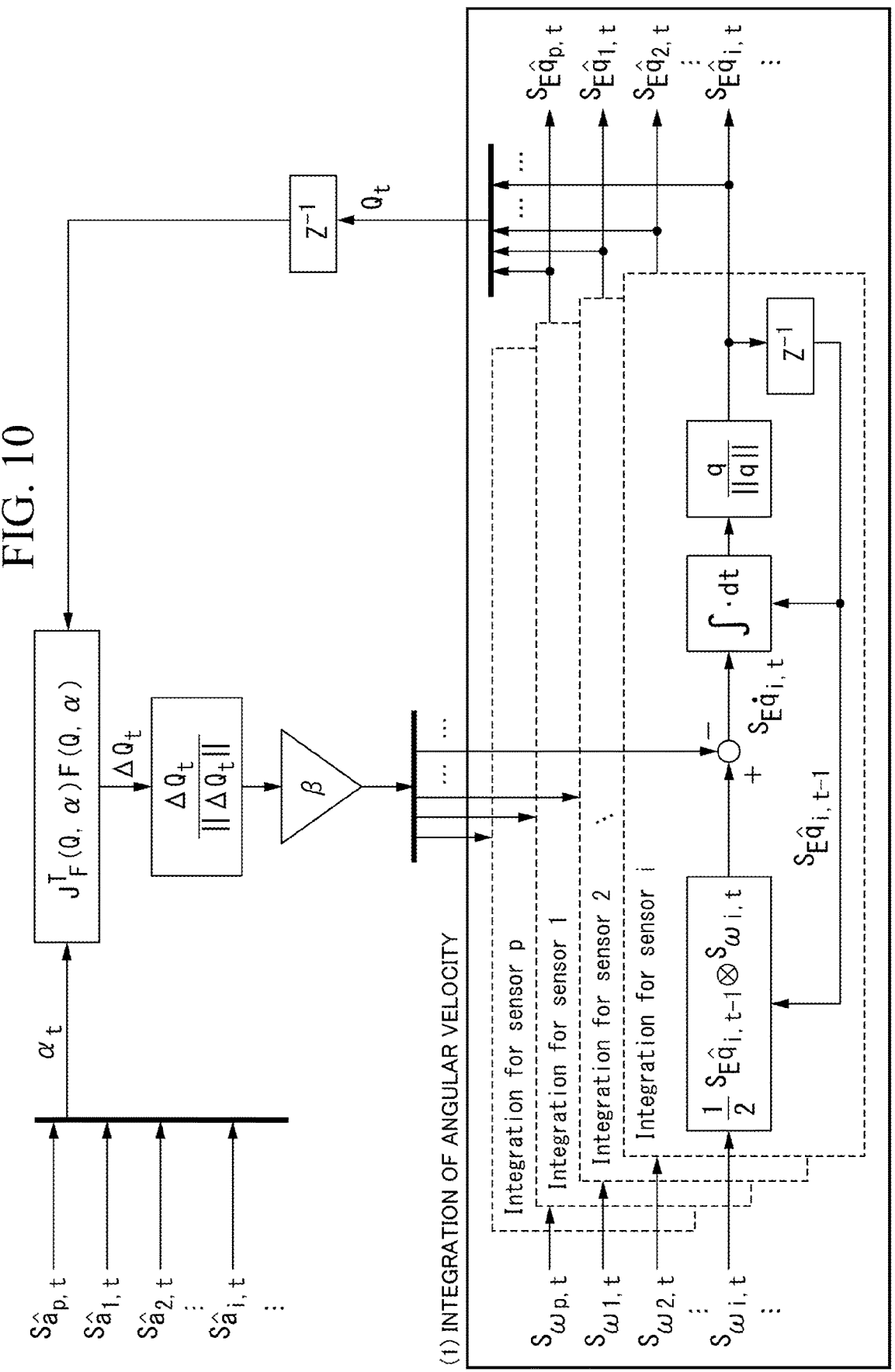
FIG. 10 is a view schematically showing a flow of the arithmetic operation processing of the whole body correction amount calculation part.
Figure 11:
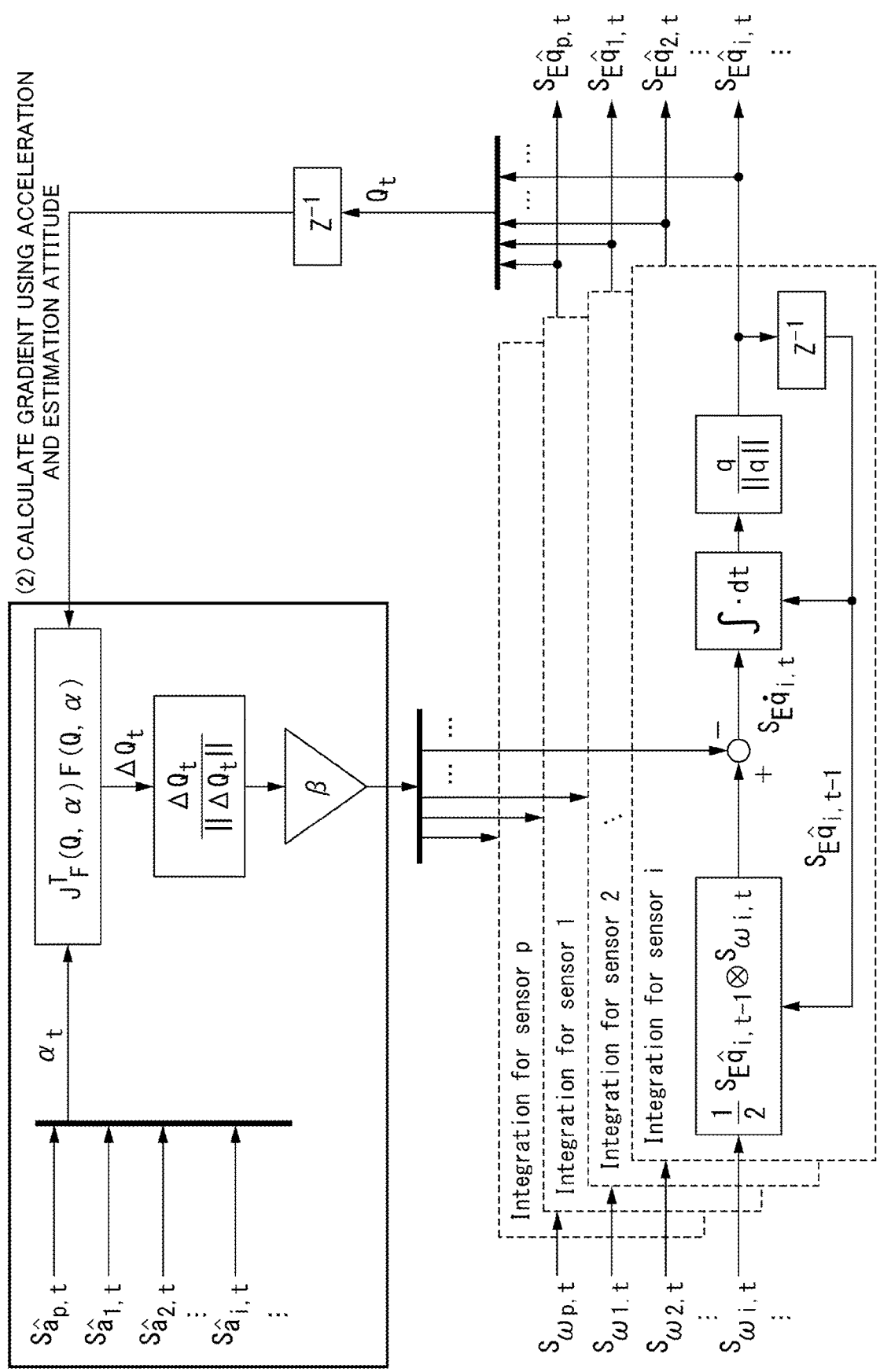
FIG. 11 is a view schematically showing a flow of the arithmetic operation processing of the whole body correction amount calculation part.
Figure 12:
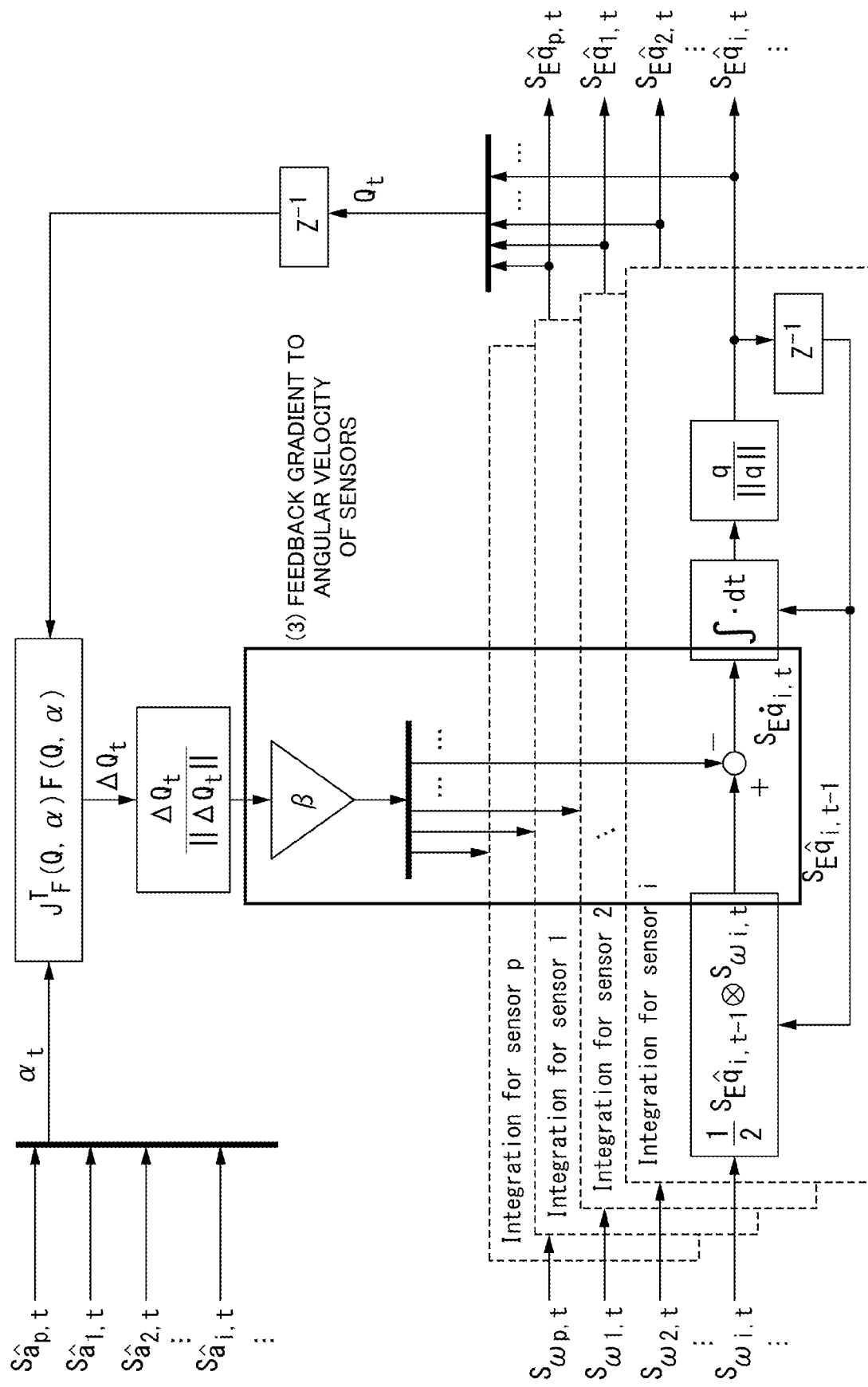
FIG. 12 is a view schematically showing a flow of the arithmetic operation processing of the whole body correction amount calculation part.

FIGS. 9 to 12 are views schematically showing flows of arithmetic operation processing of the whole body correction amount calculation part 144. FIG. 9 is a view schematically showing the whole body correction amount calculation part 144 as a whole. FIG. 10 to FIG. 12 are views for describing flows of processing of the whole body correction amount calculation part 144 step by step.

As shown in FIG. 9, the acceleration collecting part 124 converts the result acquired by the acquisition part 110 of the acceleration $^S a_{i,t}$ (i may be p expressing the pelvis that is a reference area, the same applies hereinafter) of each IMU sensor JSi measured at time t into acceleration $\alpha_t$ of all IMUs of the estimation object TGT that is the collected result. In addition, an angular velocity $^S \omega_{i,t}$ of each IMU sensor JSi acquired by the acquisition part 110 and measured at time t is output to the angular velocity integrating part 132-$i$ corresponding thereto.

In addition, a processing block from $Z^{-1}$ to β shown in a right upper portion of FIG. 9 indicates that the correction part 140 derives a correction amount in the next processing cycle.

Further, in FIG. 9 to FIG. 12, when a gradient of an objective function expressed in the following Mathematical equation (33) is $\Delta Q_t$, feedback to an angular velocity $Q_t(.)$ at time t (a dot symbol is attached as an upper script of $Q_t$, and a time differential result of the estimated posture vector $Q_t$ of the whole body at time t) can be expressed as the following Mathematical equation (34). Further, β of Mathematical equation (34) is a real number of 0≤β≤1 in order to adjust a gain of a correction amount.

[Math. 18]

$$\Delta Q = J_F^T(Q, \alpha) F(Q, \alpha) \quad (33)$$

$$\dot{Q}_t \leftarrow \dot{Q}_t - \beta \frac{\Delta Q_t}{\|\Delta Q_t\|} \quad (34)$$

The whole body correction amount calculation part 144 reflects an arbitrary real number β as a correction amount to the result in which the gradient $\Delta Q$ is normalized to the angular velocity $Q_t$ (.) as expressed in Mathematical equation (34).

The integrating part 130 integrates angular velocities of the segments as shown in FIG. 10. Next, as shown in FIG. 11, the correction part 140 calculates the gradient $\Delta Q$ using the angular velocities and the estimation postures of the segments. Next, as shown FIG. 12, the correction part 140 feedbacks the derived gradient $\Delta Q$ to the angular velocities of the IMU sensors. When the acquisition part 110 acquires the next result measured by the IMU sensors JS, as shown in FIG. 10, the integrating part 130 integrates angular velocities of the segments again. In the posture estimation device 100, since properties or experimental rules of a person's body are reflected to the estimated results of the postures of the segments by performing processing of the posture estimation of the estimation object TGT through repeated processing shown in FIG. 10 to FIG. 12, accuracy of the estimated results of the posture estimation device 100 is improved.

Since the processing as shown in FIG. 10 to FIG. 12 is repeatedly performed and the estimation posture aggregating part 142 collects the integrated results of the angular velocities of the integrating part 130, the errors of the measured angular velocities of the IMU sensors JS are averaged and the estimated posture vector Q of the whole body of Equation (2) can be derived. The result obtained by calculating the correction amount in a yaw direction from the whole body posture using the properties or experimental rules of the person's body is reflected to the estimated posture vector Q of the whole body. Since the whole body posture of the person who has suppressed a drift in a yaw angle direction can be estimated by performing posture estimation of the estimation object TGT through the above-mentioned method without using geomagnetism, the whole body posture estimation with the suppressed drift in a yaw direction can be performed even in a long-term measurement.

[Processing Flow]

Figure 13:
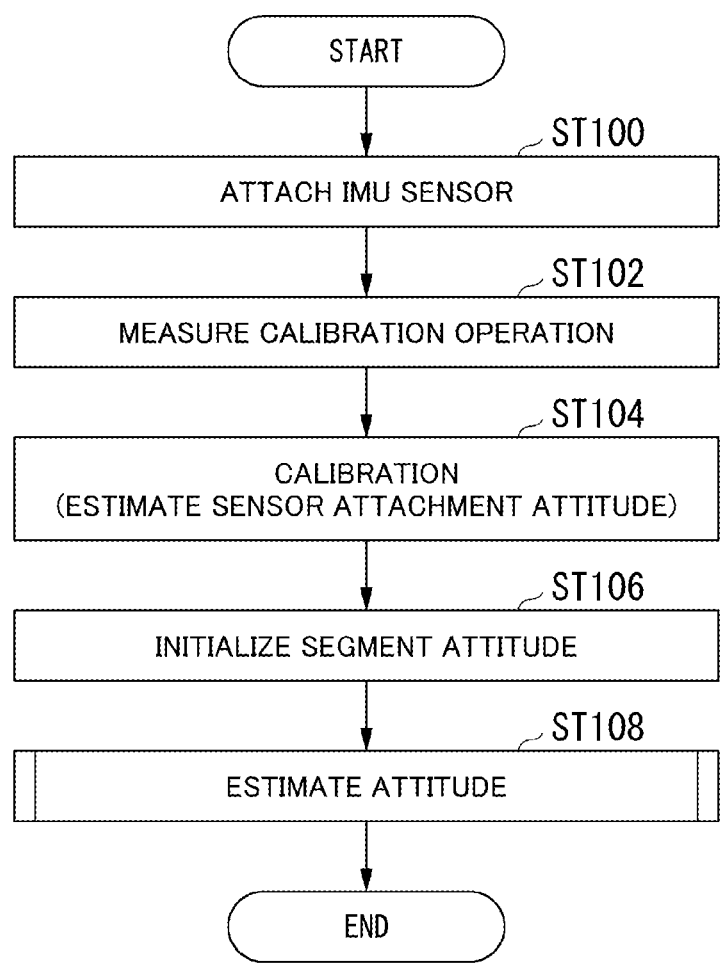
FIG. 13 is a flowchart showing an example of a flow of motion capture processing using a posture estimation device.

FIG. 13 is a flowchart showing an example of a flow of motion capture processing using the posture estimation device 100.

First, a user of the posture estimation device 100 attaches the IMU sensors to the estimation object TGT (step ST100). Next, the user of the posture estimation device 100 performs a calibration operation for a motion capture on the estimation object TGT (step S102), and performs calibration (step ST104). Next, the posture estimation device 100 performs initialization of the segment posture of the estimation object TGT (step ST106), and initializes measurement of the IMU sensors and performs processing of the posture estimation (step ST108). Further, details of the processing in step ST108 will be described using FIG. 14. Hereinabove, description of the processing of the flowchart is terminated.

Figure 14:
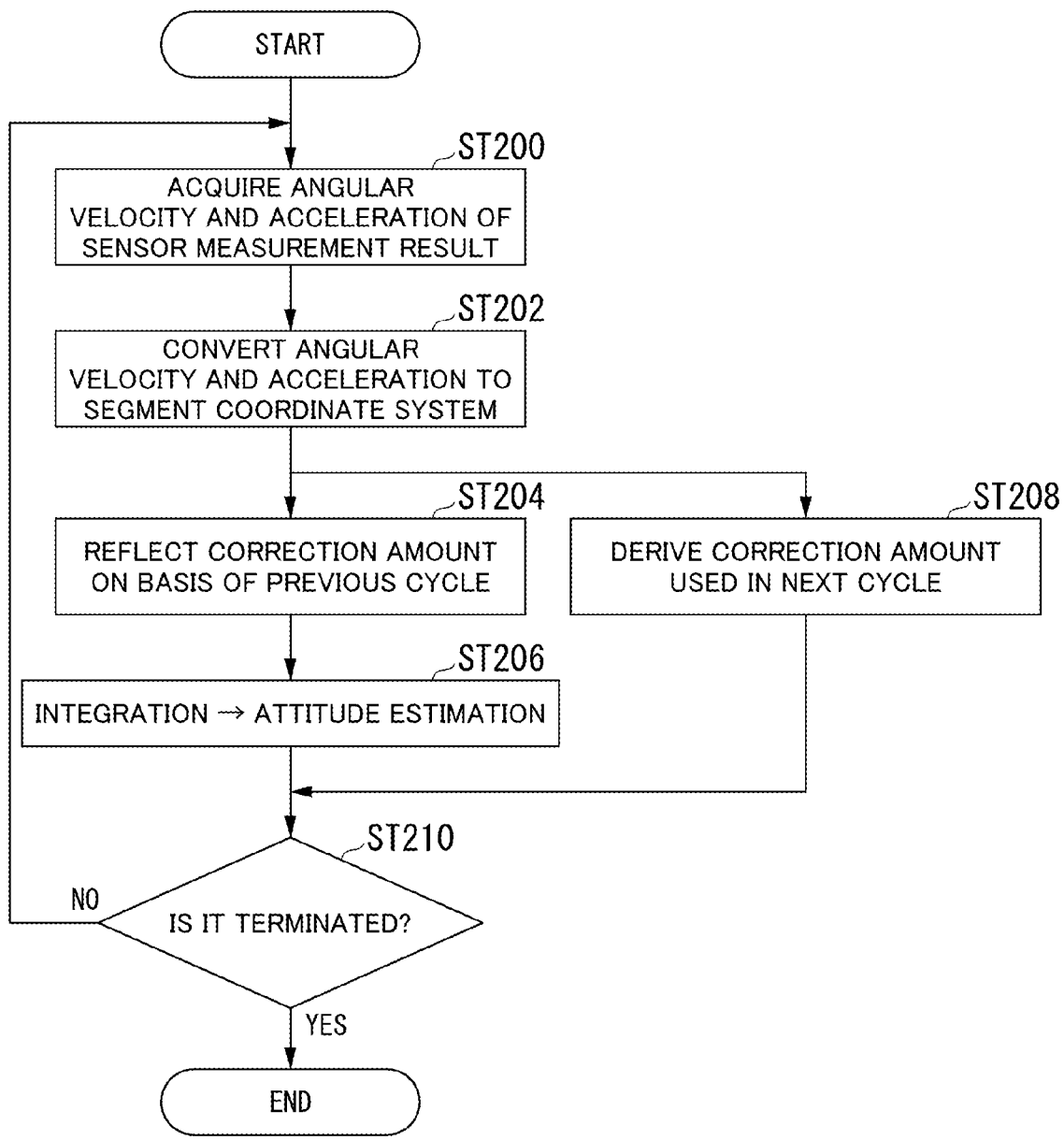
FIG. 14 is a flowchart showing an example of a flow of posture estimation processing by the posture estimation device.

FIG. 14 is a flowchart showing an example of a flow of posture estimation processing by the posture estimation device 100. First, the acquisition part 110 acquires angular velocities and accelerations that are results measured by the IMU sensors (step ST200). Next, the conversion part 120 converts the angular velocities and accelerations acquired by the acquisition part 110 to the segment coordinate system (step ST202).

Next, the correction part 140 corrects the derived correction amount in the previous processing cycle by reflecting the derived correction amount to the angular velocity of the result processed in step ST202 (step ST204). Next, the integrating part 130 performs the posture estimation of the estimation object TGT by integrating the angular velocities that are results processed in step ST204 (step ST206).

In addition, after processing in step ST202, the correction part 140 performs derivation of the gradient $\Delta Q$ of the objective function that is a correction amount using the next processing cycle (step ST208). The correction amount derived in step ST208 is used in step ST204 in the next processing cycle.

After processing in step ST206 and step ST208, the acquisition part 110 determines whether the result measured by the next IMU sensor JS is acquired (i.e., whether the processing cycle is terminated). The acquisition part 110 determines that the processing cycle is not terminated and returns to the processing in step ST200 when the result measured by the next IMU sensor is acquired. The acquisition part 110 determines that the processing cycle is terminated and terminates the processing of the flowchart in a case the state in which the result measured by the next IMU sensor is not acquired is maintained for a predetermined time or more (or when an input of an instruction showing termination of measurement by the user of the posture estimation device 100 is received).

According to the above-mentioned embodiment, more accurate posture estimation can be accomplished by performing posture estimation of the segments that are reference area from the acceleration and the angular velocities measured by the IMU sensors JS using the posture of the pelvis of the estimation object TGT that is the reference area as standard.

Hereinabove, while the aspect provided to perform the present invention has been described using the embodiment, the present invention is not limited to the embodiment, and various modifications and substitutions may be added without departing from the scope of the present invention.

For example, estimation by mechanical learning may be performed in derivation processing of the representative plane and derivation processing of the direction vectors vi of the segments by the correction part 140.

In addition, for example, one or more vectors other than the direction of gravity, geomagnetism, or the like, may be used as a direction to be standard used when the correction part 140 solves the optimization problem. When the vector other than the gravity or geomagnetism is used as the standard, for example, vectors in a forward direction of the pelvis that is the reference area and an upward/downward direction from the pelvis that is the reference area of the estimation object TGT are defined and used for correction.

While preferred embodiments of the invention have been described and illustrated above, it should be understood that these are exemplary of the invention and are not to be considered as limiting. Additions, omissions, substitutions, and other modifications can be made without departing from the scope of the present invention. Accordingly, the invention is not to be considered as being limited by the foregoing description, and is only limited by the scope of the appended claims.

What is claimed is:

1. A posture estimation device comprising:
    an acquisition part that is configured to acquire information of angular velocities and accelerations from a plurality of sensors configured to detect angular velocities and accelerations, the plurality of sensors being attached to a plurality of locations on an estimation object which is a human, an animal, or a robot having joints with a limited motion range;
    a conversion part configured to convert information acquired by the acquisition part into information of a standard coordinate system from a sensor coordinate system;
    an integrating part configured to calculate an orientation of a reference area of the estimation object to which the sensors are attached as a part of a posture of the estimation object by integrating the converted angular velocities; and
    a correction part, assuming a representative plane passing through the reference area included in the estimation object, configured to correct the converted angular velocities of the reference area so that a normal line of the representative plane and the orientation of the reference area calculated by the integrating part approaches to directions that are perpendicular to each other,
    wherein processing of the integrating part and the correction part are repeatedly performed in each processing cycle, and
    the correction part increases a degree of correcting the converted angular velocity of the reference area according to a length of a separation time in which a separation of an orientation of the reference area, which is calculated by the integrating part in a previous processing cycle, from an orientation which is perpendicular with respect to the normal line of the representative plane is continued.

2. The posture estimation device according to claim 1, wherein the correction part corrects the converted angular velocity of the reference area so as to reduce an inner product of the normal line of the representative plane and the orientation of the reference area calculated by the integrating part.

3. The posture estimation device according to claim 1, wherein the correction part further corrects the converted angular velocity of the reference area so as to reduce a separation between (i) an assumed gravity acceleration direction of each reference area derived from an orientation of the calculated reference area by the integrating part and (ii) a measured gravity acceleration direction of each reference area recognized on the basis of information of an acceleration acquired by the acquisition part.

4. A posture estimation method performed by a computer, the method comprising:
    acquiring information of angular velocities and accelerations from a plurality of sensors that are attached to a plurality of locations on an estimation object which is a human, an animal, or a robot having joints with a limited motion range and that are configured to detect angular velocities and accelerations;
    converting the acquired information into information of a standard coordinate system from a sensor coordinate system;
    calculating an orientation of a reference area of the estimation object to which the sensors are attached as a part of a posture of the estimation object by integrating the converted angular velocities; and
    assuming a representative plane passing through a reference area included in the estimation object and correcting the converted angular velocities of the reference area so that a normal line of the representative plane and an orientation of the calculated reference area approaches to directions that are perpendicular to each other,
    wherein the calculating and the assuming are repeatedly performed in each processing cycle, and
    the assuming increases a degree of correcting the converted angular velocity of the reference area according to a length of a separation time in which a separation of an orientation of the reference area, which is calculated during the calculating in a previous processing cycle, from an orientation which is perpendicular with respect to the normal line of the representative plane is continued.

5. A computer-readable non-transient storage medium, on which a posture estimation program is stored, and configured to cause a computer to:
    acquire information of angular velocities and accelerations from a plurality of sensors that are attached to a plurality of locations on an estimation object which is a human, an animal, or a robot having joints with a limited motion range and that are configured to detect angular velocities and accelerations;
    convert the acquired information into information of a standard coordinate system from a sensor coordinate system;
    calculate an orientation of a reference area of the estimation object to which the sensors are attached as a part of a posture of the estimation object by integrating the converted angular velocities; and assume a representative plane passing through a reference area included in the estimation object and correct the converted angular velocities of the reference area so that a normal line of the representative plane and an orientation of the calculated reference area approaches to directions that are perpendicular to each other, wherein the calculate the orientation and the assume a representative plane are repeatedly performed in each processing cycle, and the assuming of the representative plane increases a degree of correcting the converted angular velocity of the reference area according to a length of a separation time in which a separation of an orientation of the reference area, which is calculated during the calculation of the orientation in a previous processing cycle, from an orientation which is perpendicular with respect to the normal line of the representative plane is continued.

* * * * *